US008389682B2

(12) United States Patent
Arrecubieta et al.

(10) Patent No.: US 8,389,682 B2
(45) Date of Patent: Mar. 5, 2013

(54) INHIBITING STAPHYLOCOCCUS EPIDERMIDIS INFECTIONS

(75) Inventors: Carlos Arrecubieta, New York, NY (US); Mei-Ho Lee, New York, NY (US); Franklin D. Lowy, Hastings-on-Hudson, NY (US)

(73) Assignee: Trustees of Columbia University in the City of New York, New York, NY (US)

( * ) Notice: Subject to any disclaimer, the term of this patent is extended or adjusted under 35 U.S.C. 154(b) by 319 days.

(21) Appl. No.: 12/523,425

(22) PCT Filed: Jan. 16, 2008

(86) PCT No.: PCT/US2008/000562
§ 371 (c)(1),
(2), (4) Date: Dec. 10, 2009

(87) PCT Pub. No.: WO2008/088822
PCT Pub. Date: Jul. 24, 2008

(65) Prior Publication Data
US 2011/0117099 A1    May 19, 2011

Related U.S. Application Data

(60) Provisional application No. 60/885,098, filed on Jan. 16, 2007.

(51) Int. Cl.
*A61K 39/40* (2006.01)
(52) U.S. Cl. .................... 530/350; 424/93.2; 424/139.1; 424/243.1
(58) Field of Classification Search .................. None
See application file for complete search history.

(56) References Cited

U.S. PATENT DOCUMENTS

| 6,635,473 | B1 * | 10/2003 | Foster et al. ............... 435/320.1 |
| 6,703,025 | B1 * | 3/2004 | Patti et al. .................. 424/243.1 |
| 6,703,492 | B1 * | 3/2004 | Kimmerly .................... 536/23.1 |
| 7,473,762 | B2 * | 1/2009 | Foster et al. .................. 530/350 |
| 7,666,438 | B1 * | 2/2010 | Patti et al. .................. 424/243.1 |
| 7,709,008 | B2 * | 5/2010 | Foster et al. ............... 424/243.1 |
| 8,017,133 | B2 * | 9/2011 | Patti et al. .................. 424/243.1 |
| 2004/0038327 | A1 | 2/2004 | Foster et al. |
| 2004/0141997 | A1 | 7/2004 | Foster et al. |

FOREIGN PATENT DOCUMENTS

| WO | WO-0012689 A1 | 3/2000 |
| WO | WO-02074324 A1 | 9/2002 |
| WO | WO-2004110367 A2 | 12/2004 |
| WO | WO-2006138627 A2 | 12/2006 |
| WO | WO-2008088822 A1 | 7/2008 |

OTHER PUBLICATIONS

Ponnuraj, K et al, Cell, vol. 115, pp. 217-228, Oct. 17, 2003, A "dock, lock and latch" Structural Model for a Staphylococcal Adhesin Binding to Fibrinogen.*
Sakinc, Turkan, Bochum 2001, Dissertation, Identifizierun and Charakterisierung eines Sdr-Proteins von *Staphylococcus saprophyticus*, cover sheet (p. 1), and Sequence Alignments of SdrF-B1, 2, 3 as shown in the Figure on p. 60 (1 page, numbered p. 60).*
McCrea, K. W., et al., "The serine-aspartate repeat (Sdr) protein family in *Staphylococcus epidermidis*", *Microbiology*, 146, (2000), 1535-1546.

(Continued)

*Primary Examiner* — Albert Navarro
*Assistant Examiner* — Ginny Portner
(74) *Attorney, Agent, or Firm* — Schwegman Lundberg Woessner P.A.

(57) ABSTRACT

The invention relates to *Staphylococcus epidermidis* peptides, antibodies and nucleic acids that can inhibit *Staphylococcus epidermidis* infection of a mammalian subject and colonization of a medical device in the mammal.

5 Claims, 12 Drawing Sheets

OTHER PUBLICATIONS

"International Application Serial No. PCT/US2008/000562, Search Report mailed Jun. 23, 2008", 10 pgs.

"International Application Serial No. PCT/US2008/000562, Written Opinion mailed Jun. 23, 2008", 9 pgs.

Arrecubieta, C., et al., "SdrF mediates *Staphylococcus epidermidis* adherence to ventricular assist device transcutaneous drivelines", Absracts of the General Meeting of the American society for microbiology, vol. 106,, (May 22, 2006), 38-39 pgs.

Arrecubieta, C., et al., "Srdf, a *Staphylococcus epidermidis* surface protein, binds type I collagen", Journal of Biological Chemistry, vol. 282(26), (Jun. 2007), 18767-18776.

Bowden, M. G, et al., "Identification & preliminary characterization of cell-wall-anchored proteins of *Staphylococcus epidermidis*", Microbiology,society for general microbiology, reading,GB,vol. 151(5), (May 1, 2005), 1453-1464 pgs.

Que, Y., et al., "Expression of *Staphylococcus aureus* clumping factor A in *Lactococcus lactis* subsp. *cremoris* using a new shuttle vector", Infection & Immunity, vol. 68.(6), (Jun. 2000), 3516-3522.

Sakinc, Turkan, et al., "SdrI, a serine-aspartate repeat protein indentified in *Staphylococcus saprophyticus* strain 7108, is a collagen-binding protein", Infection & Immunity,vol. 74(8), (Aug. 2006), 4615-4623.

* cited by examiner

*FIG. 1*
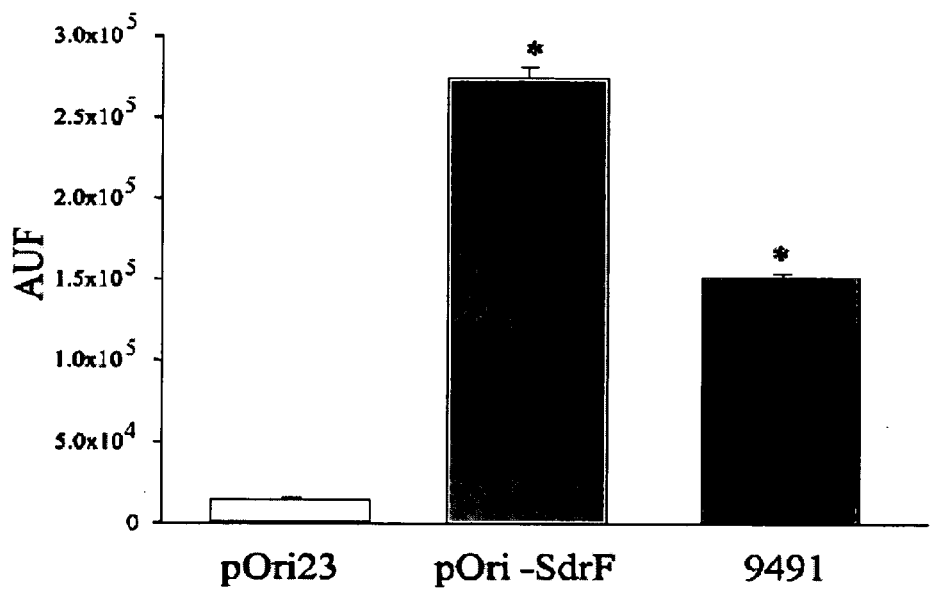
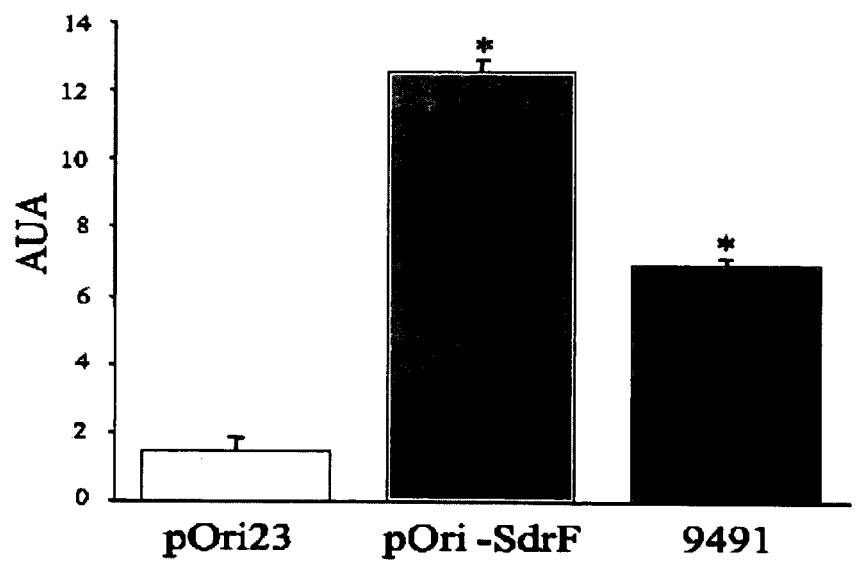

FIG. 2
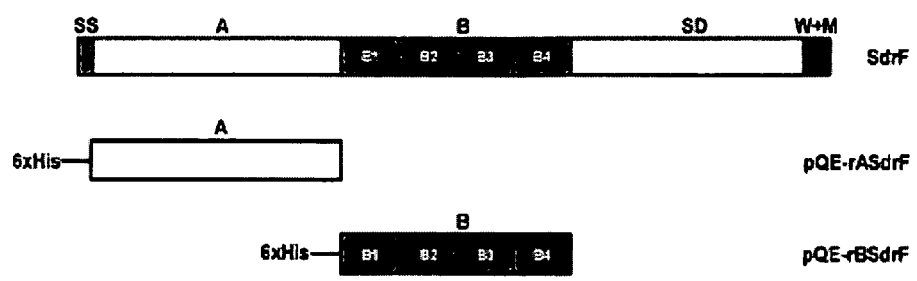
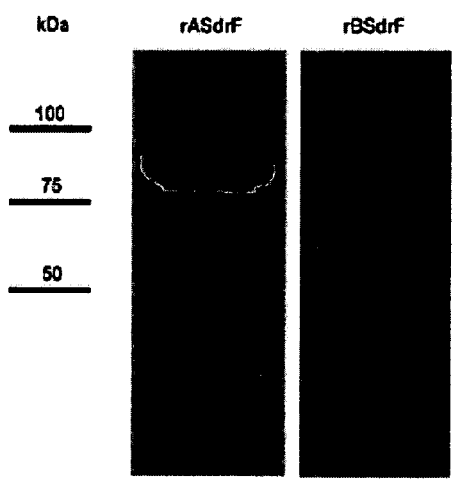

FIG. 3
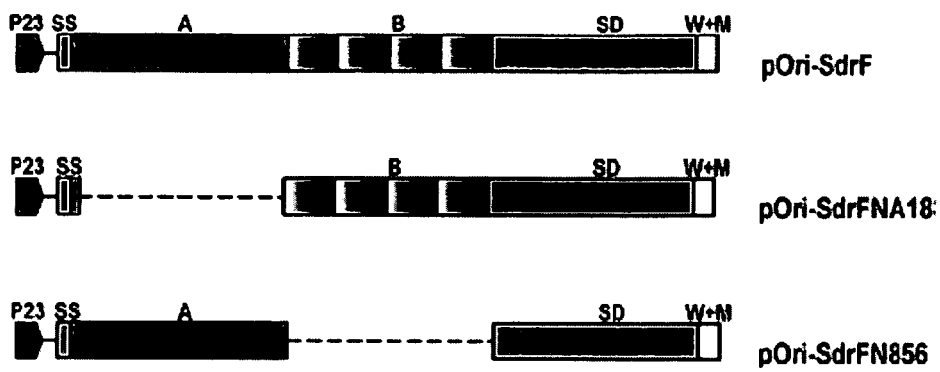
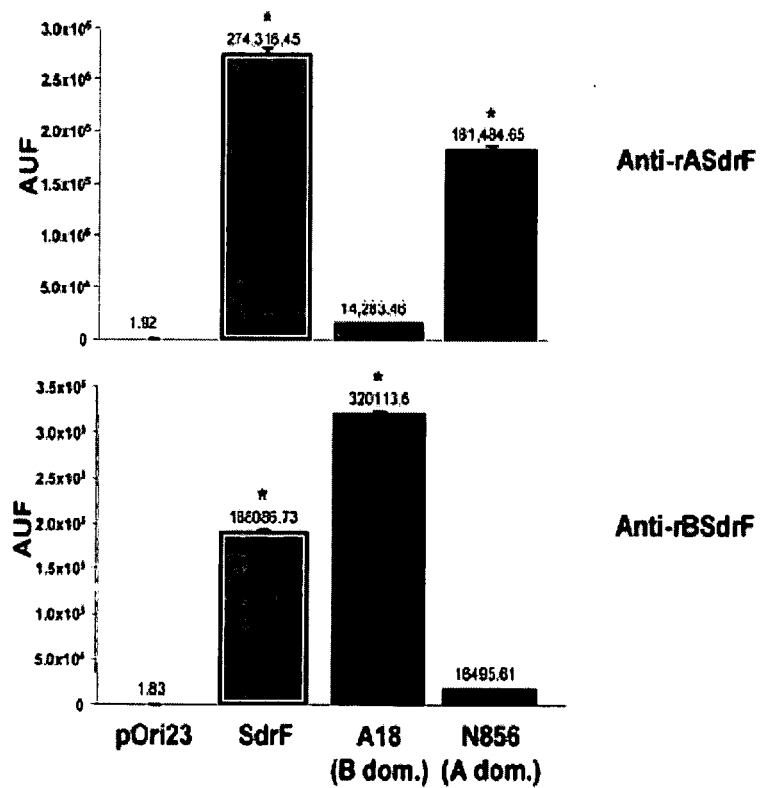

FIG. 3(con't)
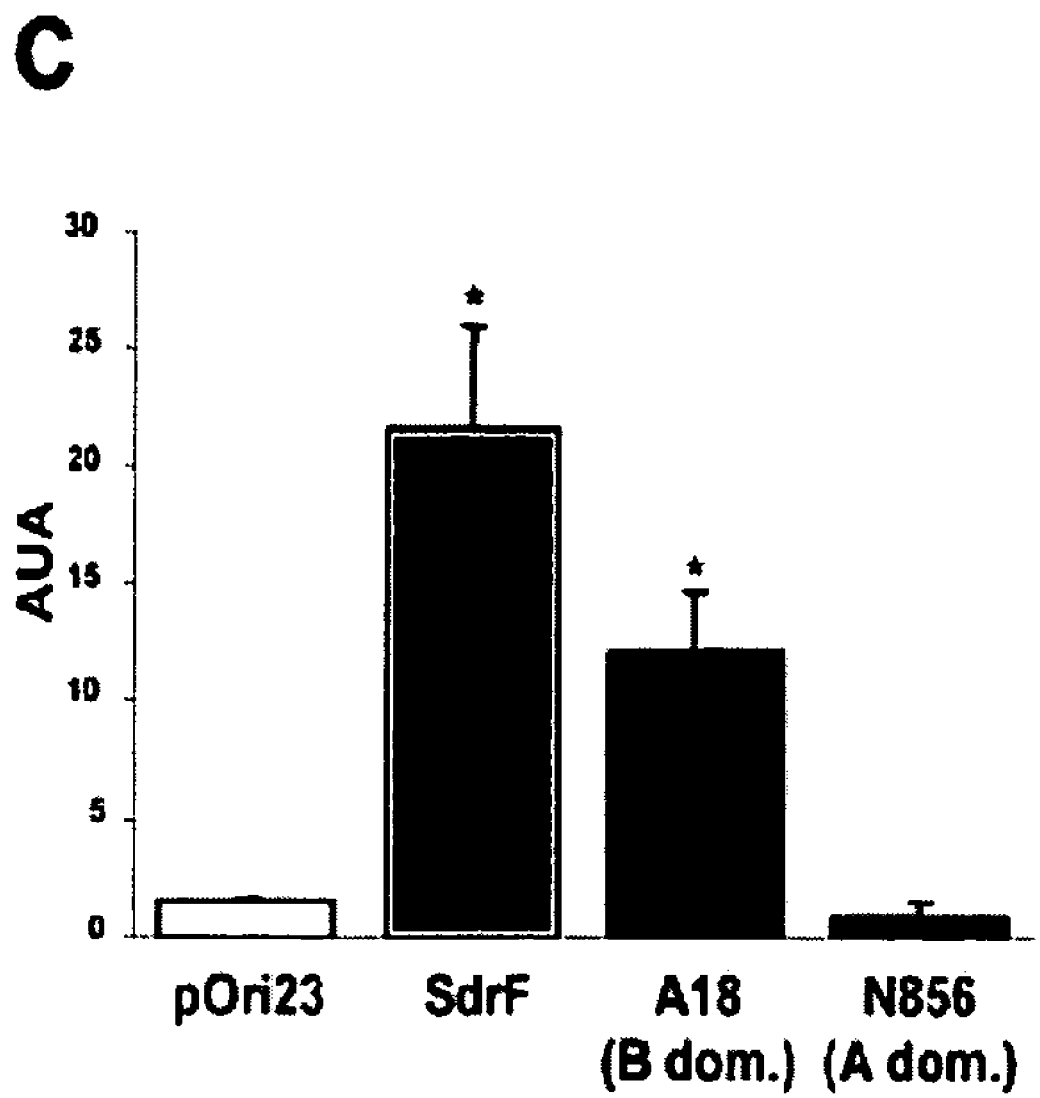

FIG. 6
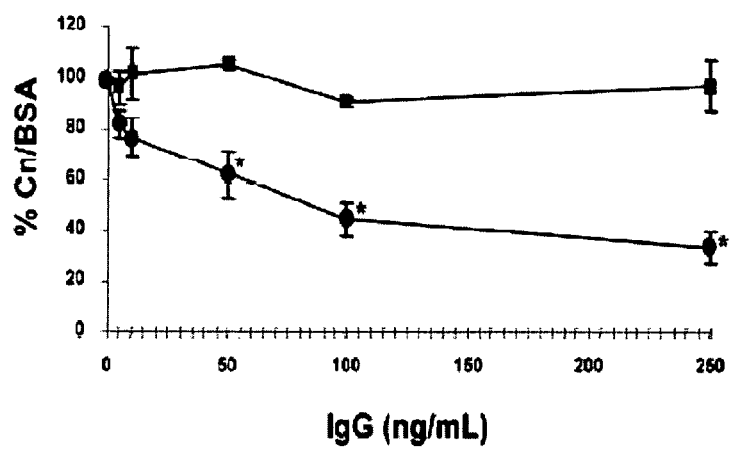
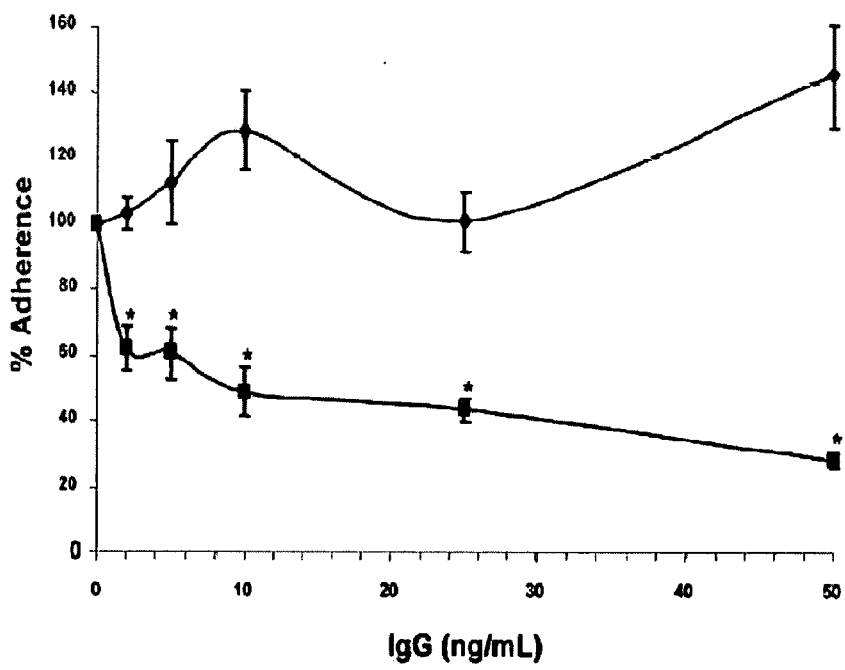

FIG. 10

| | RBS | | | | | | | | | | | | | |
|---|---|---|---|---|---|---|---|---|---|---|---|---|---|---|
| SE 9491 | tgg | agg | tat | agt | M<br>atg | K<br>aaa | K<br>aag | R<br>aga | R<br>aga | Q<br>caa | G<br>gga | P<br>cca | I<br>att | N<br>aac | K<br>aag | (SEQ ID NO: 29)
| SE 9 | tgg | agg | tat | agt | M<br>atg | K<br>aaa | K<br>aag | R<br>aga | R<br>aga | Q<br>caa | G<br>gga | P<br>cca | I<br>att | N<br>aac | K<br>aag | (SEQ ID NO: 28)

| | | | | | | | | | | | | | | |
|---|---|---|---|---|---|---|---|---|---|---|---|---|---|---|
| SE 9491 | R<br>aga | V<br>gtg | D<br>gat | F<br>ttt | L<br>cta | S<br>tcc | N<br>aac | K<br>aag | V<br>gta | N<br>aac | K<br>aag | Y<br>tac | S<br>tcg | I<br>att | R<br>agg | (SEQ ID NO: 29 con't)
| SE 9 | R<br>aga | V<br>gtg | D<br>gat | F<br>ttt | L<br>cta | S<br>tcc | N<br>aac | K<br>aag | V<br>gta | N<br>aac | K<br>aag | Y<br>tac | stop<br>tAg | I<br>att | R<br>agg | (SEQ ID NO: 28 con't)

(SEQ ID NO: 33)
(SEQ ID NO: 32)
(SEQ ID NO: 33 con't)
(SEQ ID NO: 32 con't)

SEQUENCE LISTING

<160> NUMBER OF SEQ ID NOS: 33

<210> SEQ ID NO 1
<211> LENGTH: 1733
<212> TYPE: PRT
<213> ORGANISM: Staphylococcus epidermidis

<400> SEQUENCE: 1

```
Met Lys Lys Arg Arg Gln Gly Pro Ile Asn Lys Arg Val Asp Phe Leu
  1               5                  10                  15

Ser Asn Lys Val Asn Lys Tyr Ser Ile Arg Lys Phe Thr Val Gly Thr
                 20                  25                  30

Ala Ser Ile Leu Val Gly Ala Thr Leu Met Phe Gly Ala Ala Asp Asn
             35                  40                  45

Glu Ala Lys Ala Ala Glu Asp Asn Gln Leu Glu Ser Ala Ser Lys Glu
 50                  55                  60

Glu Gln Lys Gly Ser Arg Asp Asn Glu Asn Ser Lys Leu Asn Gln Val
 65                  70                  75                  80

Asp Leu Asp Asn Gly Ser His Ser Ser Glu Lys Thr Thr Asn Val Asn
                 85                  90                  95

Asn Ala Thr Glu Val Lys Lys Val Glu Ala Pro Thr Thr Ser Asp Val
            100                 105                 110

Ser Lys Pro Lys Ala Asn Glu Ala Val Val Thr Asn Glu Ser Thr Lys
        115                 120                 125

Pro Lys Thr Thr Glu Ala Pro Thr Val Asn Glu Glu Ser Ile Ala Glu
    130                 135                 140

Thr Pro Lys Thr Ser Thr Thr Gln Gln Asp Ser Thr Glu Lys Asn Asn
145                 150                 155                 160

Pro Ser Leu Lys Asp Asn Leu Asn Ser Ser Thr Thr Ser Lys Glu
                165                 170                 175

Ser Lys Thr Asp Glu His Ser Thr Lys Gln Ala Gln Met Ser Thr Asn
                180                 185                 190

Lys Ser Asn Leu Asp Thr Asn Asp Ser Pro Thr Gln Ser Glu Lys Thr
        195                 200                 205

Ser Ser Gln Ala Asn Asn Asp Ser Thr Asp Asn Gln Ser Ala Pro Ser
    210                 215                 220

Lys Gln Leu Asp Ser Lys Pro Ser Glu Gln Lys Val Tyr Lys Thr Lys
225                 230                 235                 240

Phe Asn Asp Glu Pro Thr Gln Asp Val Glu His Thr Thr Thr Lys Leu
                245                 250                 255

Lys Thr Pro Ser Val Ser Thr Ser Ser Val Asn Asp Lys Gln Asp
                260                 265                 270

Tyr Thr Arg Ser Ala Val Ala Ser Leu Gly Val Asp Ser Asn Glu Thr
        275                 280                 285

Glu Ala Ile Thr Asn Ala Val Arg Asp Asn Leu Asp Leu Lys Ala Ala
    290                 295                 300

Ser Arg Glu Gln Ile Asn Glu Ala Ile Ile Ala Glu Ala Leu Lys Lys
305                 310                 315                 320

Asp Phe Ser Asn Pro Asp Tyr Gly Val Asp Thr Pro Leu Ala Leu Asn
                325                 330                 335

Arg Ser Gln Ser Lys Asn Ser Pro His Lys Ser Ala Ser Pro Arg Met
                340                 345                 350

Asn Leu Met Ser Leu Ala Ala Glu Pro Asn Ser Gly Lys Asn Val Asn
                355                 360                 365
```

```
Asp Lys Val Lys Ile Thr Asn Pro Thr Leu Ser Leu Asn Lys Ser Asn
    370                 375                 380

Asn His Ala Asn Asn Val Ile Trp Pro Thr Ser Asn Glu Gln Phe Asn
385                 390                 395                 400

Leu Lys Ala Asn Tyr Glu Leu Asp Asp Ser Ile Lys Glu Gly Asp Thr
                405                 410                 415

Phe Thr Ile Lys Tyr Gly Gln Tyr Ile Arg Pro Gly Gly Leu Glu Leu
            420                 425                 430

Pro Ala Ile Lys Thr Gln Leu Arg Ser Lys Asp Gly Ser Ile Val Ala
            435                 440                 445

Asn Gly Val Tyr Asp Lys Thr Thr Asn Thr Thr Tyr Thr Phe Thr
        450                 455                 460

Asn Tyr Val Asp Gln Tyr Gln Asn Ile Thr Gly Ser Phe Asp Leu Ile
465                 470                 475                 480

Ala Thr Pro Lys Arg Glu Thr Ala Ile Lys Asp Asn Gln Asn Tyr Pro
                485                 490                 495

Met Glu Val Thr Ile Ala Asn Glu Val Val Lys Lys Asp Phe Ile Val
            500                 505                 510

Asp Tyr Gly Asn Lys Lys Asp Asn Thr Thr Ala Ala Val Ala Asn
        515                 520                 525

Val Asp Asn Val Asn Asn Lys His Asn Glu Val Val Tyr Leu Asn Gln
530                 535                 540

Asn Asn Gln Asn Pro Lys Tyr Ala Lys Tyr Phe Ser Thr Val Lys Asn
545                 550                 555                 560

Gly Glu Phe Ile Pro Gly Glu Val Lys Val Tyr Glu Val Thr Asp Thr
            565                 570                 575

Asn Ala Met Val Asp Ser Phe Asn Pro Asp Leu Asn Ser Ser Asn Val
            580                 585                 590

Lys Asp Val Thr Ser Gln Phe Ala Pro Lys Val Ser Ala Asp Gly Thr
        595                 600                 605

Arg Val Asp Ile Asn Phe Ala Arg Ser Met Ala Asn Gly Lys Lys Tyr
    610                 615                 620

Ile Val Thr Gln Ala Val Arg Pro Thr Gly Thr Gly Asn Val Tyr Thr
625                 630                 635                 640

Glu Tyr Trp Leu Thr Arg Asp Gly Thr Thr Asn Thr Asn Asp Phe Tyr
                645                 650                 655

Arg Gly Thr Lys Ser Thr Thr Val Thr Tyr Leu Asn Gly Ser Ser Thr
            660                 665                 670

Ala Gln Gly Asp Asn Pro Thr Tyr Ser Leu Gly Asp Tyr Val Trp Leu
        675                 680                 685

Asp Lys Asn Lys Asn Gly Val Gln Asp Asp Glu Lys Gly Leu Ala
    690                 695                 700

Gly Val Tyr Val Thr Leu Lys Asp Ser Asn Asn Arg Glu Leu Gln Arg
705                 710                 715                 720

Val Thr Thr Asp Gln Ser Gly His Tyr Gln Phe Asp Asn Leu Gln Asn
                725                 730                 735

Gly Thr Tyr Thr Val Glu Phe Ala Ile Pro Asp Asn Tyr Thr Pro Ser
            740                 745                 750

Pro Ala Asn Asn Ser Thr Asn Asp Ala Ile Asp Ser Asp Gly Glu Arg
        755                 760                 765

Asp Gly Thr Arg Lys Val Val Val Ala Lys Gly Thr Ile Asn Asn Ala
    770                 775                 780

Asp Asn Met Thr Val Asp Thr Gly Phe Tyr Leu Thr Pro Lys Tyr Asn
```

-continued

```
                785                 790                 795                 800
Val Gly Asp Tyr Val Trp Glu Asp Thr Asn Lys Asp Gly Ile Gln Asp
                    805                 810                 815

Asp Asn Glu Lys Gly Ile Ser Gly Val Lys Val Thr Leu Lys Asn Lys
                820                 825                 830

Asn Gly Asp Thr Ile Gly Thr Thr Thr Asp Ser Asn Gly Lys Tyr
                835                 840                 845

Glu Phe Thr Gly Leu Glu Asn Gly Asp Tyr Thr Ile Glu Phe Glu Thr
            850                 855                 860

Pro Glu Gly Tyr Thr Pro Thr Lys Gln Asn Ser Gly Ser Asp Glu Gly
865                 870                 875                 880

Lys Asp Ser Asn Gly Thr Lys Thr Thr Val Thr Val Lys Ala Asp
                    885                 890                 895

Asn Lys Thr Ile Asp Ser Gly Phe Tyr Lys Pro Thr Tyr Asn Leu Gly
                900                 905                 910

Asp Tyr Val Trp Glu Asp Thr Asn Lys Asp Gly Ile Gln Asp Ser
                915                 920                 925

Glu Lys Gly Ile Ser Gly Val Lys Val Thr Leu Lys Asp Lys Asn Gly
            930                 935                 940

Asn Ala Ile Gly Thr Thr Thr Asp Ala Ser Gly His Tyr Gln Phe
945                 950                 955                 960

Lys Gly Leu Glu Asn Gly Ser Tyr Thr Val Glu Phe Glu Thr Pro Ser
                    965                 970                 975

Gly Tyr Thr Pro Thr Lys Ala Asn Ser Gly Gln Asp Ile Thr Val Asp
                980                 985                 990

Ser Asn Gly Ile Thr Thr Thr Gly Ile Ile Asn Gly Ala Asp Asn Leu
                995                 1000                1005

Thr Ile Asp Ser Gly Phe Tyr Lys Thr Pro Lys Tyr Ser Val Gly Asp
            1010                1015                1020

Tyr Val Trp Glu Asp Thr Asn Lys Asp Gly Ile Gln Asp Asp Asn Glu
1025                1030                1035                1040

Lys Gly Ile Ser Gly Val Lys Val Thr Leu Lys Asp Glu Lys Gly Asn
                    1045                1050                1055

Ile Ile Ser Thr Thr Thr Thr Asp Glu Asn Gly Lys Tyr Gln Phe Asp
                1060                1065                1070

Asn Leu Asp Ser Gly Asn Tyr Ile Ile His Phe Glu Lys Pro Glu Gly
            1075                1080                1085

Met Thr Gln Thr Thr Ala Asn Ser Gly Asn Asp Asp Glu Lys Asp Ala
                    1090                1095                1100

Asp Gly Glu Asp Val Arg Val Thr Ile Thr Asp His Asp Asp Phe Ser
1105                1110                1115                1120

Ile Asp Asn Gly Tyr Phe Asp Asp Ser Asp Ser Asp Ser Asp Ala
                    1125                1130                1135

Asp Ser Asp Ser Asp Ser Asp Ser Asp Ala Ser Asp Ser
            1140                1145                1150

Asp Ala Asp Ser Asp Ser Asp Ala Asp Ser Asp Ser Asp Ser Asp Ser
                1155                1160                1165

Asp Ser Asp Ala Asp Ser Asp Ser Asp Ser Asp Ser Asp Ser
                1170                1175                1180

Asp Ser Asp Ser Asp Ala Asp Ser Asp Ser Asp Ser Asp Ser Asp Ser
1185                1190                1195                1200

Asp Ala Asp Ser Asp Ser Asp Ser Asp Ser Asp Ser Asp Ser
                    1205                1210                1215
```

-continued

Asp Ser Asp Ser Asp Ser Asp Ser Asp Ser Asp Ser Asp Ser
            1220                1225                1230

Asp Ser Asp Ser Asp Ser Asp Ser Asp Ser Asp Ala Asp Ser
        1235                1240                1245

Asp Ser Asp Ala Asp Ser Asp Ser Asp Ser Asp Ser Asp Ala
        1250                1255                1260

Asp Ser Asp Ser Asp Ser Asp Ser Asp Ala Asp Ser Asp Ser
1265                1270                1275                1280

Asp Ser Asp Ser Asp Ser Asp Ser Asp Ser Asp Ala Asp Ser
            1285                1290                1295

Asp Ser Asp Ser Asp Ser Asp Ser Asp Ser Asp Ser Asp Ser
            1300                1305                1310

Asp Ser Asp Ser Asp Ser Asp Ser Asp Ala Asp Ser Asp Ser
            1315                1320                1325

Asp Ser Asp Ser Asp Ser Asp Ser Asp Ser Asp Ser Asp Ser
            1330                1335                1340

Asp Ser Asp Ser Asp Ser Asp Ser Asp Ala Asp Ser Asp Ala Asp Ser
1345                1350                1355                1360

Asp Ser Asp Ala Asp Ser Asp Ser Asp Ala Asp Ser Asp Ser Asp Ser
            1365                1370                1375

Asp Ser Asp Ser Asp Ala Asp Ser Asp Ser Asp Ser Asp Ser Asp Ser
            1380                1385                1390

Asp Ser Asp Ser Asp Ser Asp Ser Asp Ser Asp Ser Asp Ser
            1395                1400                1405

Asp Ser Asp Ser Asp Ser Asp Ser Asp Ala Asp Ser Asp Ser Asp Ser
        1410                1415                1420

Asp Ser Asp Ser Asp Ser Asp Ser Asp Ser Asp Ala Asp Ser Asp Ser
1425                1430                1435                1440

Asp Ser Asp Ser Asp Ser Asp Ala Asp Ser Asp Ser Asp Ser Asp Ser
            1445                1450                1455

Asp Ser Asp Ala Asp Ser Asp Ser Asp Ser Asp Ser Asp Ser Asp Ala
            1460                1465                1470

Asp Ser Asp Ser Asp Ser Asp Ser Asp Ser Asp Ser Asp Ser
            1475                1480                1485

Asp Ala Asp Ser Asp Ser Asp Ser Asp Ser Asp Ser Asp Ser
        1490                1495                1500

Asp Ser Asp Ser Asp Ser Asp Ser Asp Ser Asp Ser Asp Ser
1505                1510                1515                1520

Asp Ser Asp Ser Asp Ser Asp Ser Asp Ser Asp Ser Asp Ser
            1525                1530                1535

Asp Ser Asp Ser Asp Ser Asp Ser Asp Ser Asp Ser Asp Ser
            1540                1545                1550

Asp Ser Asp Ser Asp Ser Asp Ser Asp Ser Asp Ser Asp Ser
            1555                1560                1565

Asp Ser Asp Ser Asp Ser Asp Ser Asp Ser Asp Ser Asp Ser
            1570                1575                1580

Asp Ser Asp Ser Asp Ser Asp Ser Asp Ser Asp Ser Asp Ser
1585                1590                1595                1600

Asp Ser Asp Ser Asp Ser Asp Ser Asp Ser Asp Ser Asp Ser
            1605                1610                1615

Asp Ser Asp Ser Asp Ala Asp Ser Asp Ser Asp Ser Asp Ser
            1620                1625                1630

Asp Ala Asp Ser Asp Ser Asp Ser Asp Ser Asp Ser Asp Ser
            1635                1640                1645

```
Asp Ser Asp Ser Asp Ser Asp Ser Asp Ser Asp Ser
    1650            1655            1660

Asp Ser Asp Ser Asp Ser Asp Ser Asp Ser Asp Ser
1665            1670            1675            1680

Asp Ser Asp Ser Asp Ser Lys Asn Ala Lys Leu Pro Asp
            1685            1690            1695

Thr Gly Ala Asn Glu Asp His Asp Ser Lys Gly Thr Leu Leu Gly Thr
        1700            1705            1710

Leu Phe Ala Gly Leu Gly Ala Leu Leu Gly Arg Arg Lys Lys
        1715            1720            1725

Asp Asn Lys Glu Lys
    1730

<210> SEQ ID NO 2
<211> LENGTH: 625
<212> TYPE: PRT
<213> ORGANISM: Staphylococcus epidermidis

<400> SEQUENCE: 2

Ala Glu Asp Asn Gln Leu Glu Ser Ala Ser Lys Glu Gln Lys Gly
  1               5                  10                  15

Ser Arg Asp Asn Glu Asn Ser Lys Leu Asn Gln Val Asp Leu Asp Asn
            20                  25                  30

Gly Ser His Ser Ser Glu Lys Thr Thr Asn Val Asn Asn Ala Thr Glu
        35                  40                  45

Val Lys Lys Val Glu Ala Pro Thr Thr Ser Asp Val Ser Lys Pro Lys
    50                  55                  60

Ala Asn Glu Ala Val Val Thr Asn Glu Ser Thr Lys Pro Lys Thr Thr
65                  70                  75                  80

Glu Ala Pro Thr Val Asn Glu Glu Ser Ile Ala Glu Thr Pro Lys Thr
                85                  90                  95

Ser Thr Thr Gln Gln Asp Ser Thr Glu Lys Asn Asn Pro Ser Leu Lys
            100                 105                 110

Asp Asn Leu Asn Ser Ser Ser Thr Thr Ser Lys Glu Ser Lys Thr Asp
        115                 120                 125

Glu His Ser Thr Lys Gln Ala Gln Met Ser Thr Asn Lys Ser Asn Leu
    130                 135                 140

Asp Thr Asn Asp Ser Pro Thr Gln Ser Glu Lys Thr Ser Ser Gln Ala
145                 150                 155                 160

Asn Asn Asp Ser Thr Asp Asn Gln Ser Ala Pro Ser Lys Gln Leu Asp
                165                 170                 175

Ser Lys Pro Ser Glu Gln Lys Val Tyr Lys Thr Lys Phe Asn Asp Glu
            180                 185                 190

Pro Thr Gln Asp Val Glu His Thr Thr Thr Lys Leu Lys Thr Pro Ser
        195                 200                 205

Val Ser Thr Asp Ser Ser Val Asn Asp Lys Gln Asp Tyr Thr Arg Ser
    210                 215                 220

Ala Val Ala Ser Leu Gly Val Asp Ser Asn Glu Thr Glu Ala Ile Thr
225                 230                 235                 240

Asn Ala Val Arg Asp Asn Leu Asp Leu Lys Ala Ala Ser Arg Glu Gln
                245                 250                 255

Ile Asn Glu Ala Ile Ile Ala Glu Ala Leu Lys Lys Asp Phe Ser Asn
            260                 265                 270

Pro Asp Tyr Gly Val Asp Thr Pro Leu Ala Leu Asn Arg Ser Gln Ser
        275                 280                 285
```

```
Lys Asn Ser Pro His Lys Ser Ala Ser Pro Arg Met Asn Leu Met Ser
    290                 295                 300

Leu Ala Ala Glu Pro Asn Ser Gly Lys Asn Val Asn Asp Lys Val Lys
305                 310                 315                 320

Ile Thr Asn Pro Thr Leu Ser Leu Asn Lys Ser Asn Asn His Ala Asn
                325                 330                 335

Asn Val Ile Trp Pro Thr Ser Asn Glu Gln Phe Asn Leu Lys Ala Asn
            340                 345                 350

Tyr Glu Leu Asp Asp Ser Ile Lys Glu Gly Asp Thr Phe Thr Ile Lys
        355                 360                 365

Tyr Gly Gln Tyr Ile Arg Pro Gly Gly Leu Glu Leu Pro Ala Ile Lys
    370                 375                 380

Thr Gln Leu Arg Ser Lys Asp Gly Ser Ile Val Ala Asn Gly Val Tyr
385                 390                 395                 400

Asp Lys Thr Thr Asn Thr Thr Thr Tyr Thr Phe Thr Asn Tyr Val Asp
                405                 410                 415

Gln Tyr Gln Asn Ile Thr Gly Ser Phe Asp Leu Ile Ala Thr Pro Lys
            420                 425                 430

Arg Glu Thr Ala Ile Lys Asp Asn Gln Asn Tyr Pro Met Glu Val Thr
        435                 440                 445

Ile Ala Asn Glu Val Val Lys Lys Asp Phe Ile Val Asp Tyr Gly Asn
    450                 455                 460

Lys Lys Asp Asn Thr Thr Thr Ala Ala Val Ala Asn Val Asp Asn Val
465                 470                 475                 480

Asn Asn Lys His Asn Glu Val Val Tyr Leu Asn Gln Asn Asn Gln Asn
                485                 490                 495

Pro Lys Tyr Ala Lys Tyr Phe Ser Thr Val Lys Asn Gly Glu Phe Ile
            500                 505                 510

Pro Gly Glu Val Lys Val Tyr Glu Val Thr Asp Thr Asn Ala Met Val
        515                 520                 525

Asp Ser Phe Asn Pro Asp Leu Asn Ser Ser Asn Val Lys Asp Val Thr
    530                 535                 540

Ser Gln Phe Ala Pro Lys Val Ser Ala Asp Gly Thr Arg Val Asp Ile
545                 550                 555                 560

Asn Phe Ala Arg Ser Met Ala Asn Gly Lys Lys Tyr Ile Val Thr Gln
                565                 570                 575

Ala Val Arg Pro Thr Gly Thr Gly Asn Val Tyr Thr Glu Tyr Trp Leu
            580                 585                 590

Thr Arg Asp Gly Thr Thr Asn Thr Asn Asp Phe Tyr Arg Gly Thr Lys
        595                 600                 605

Ser Thr Thr Val Thr Tyr Leu Asn Gly Ser Ser Thr Ala Gln Gly Asp
    610                 615                 620

Asn
625

<210> SEQ ID NO 3
<211> LENGTH: 451
<212> TYPE: PRT
<213> ORGANISM: Staphylococcus epidermidis

<400> SEQUENCE: 3

Pro Thr Tyr Ser Leu Gly Asp Tyr Val Trp Leu Asp Lys Asn Lys Asn
1               5                   10                  15

Gly Val Gln Asp Asp Glu Lys Gly Leu Ala Gly Val Tyr Val Thr
            20                  25                  30
```

```
Leu Lys Asp Ser Asn Asn Arg Glu Leu Gln Arg Val Thr Thr Asp Gln
            35                  40                  45

Ser Gly His Tyr Gln Phe Asp Asn Leu Gln Asn Gly Thr Tyr Thr Val
 50                  55                  60

Glu Phe Ala Ile Pro Asp Asn Tyr Thr Pro Pro Ala Asn Asn Ser
 65                  70                  75                  80

Thr Asn Asp Ala Ile Asp Ser Asp Gly Glu Arg Asp Gly Thr Arg Lys
                85                  90                  95

Val Val Val Ala Lys Gly Thr Ile Asn Asn Ala Asp Asn Met Thr Val
                100                 105                 110

Asp Thr Gly Phe Tyr Leu Thr Pro Lys Tyr Asn Val Gly Asp Tyr Val
                115                 120                 125

Trp Glu Asp Thr Asn Lys Asp Gly Ile Gln Asp Asn Glu Lys Gly
            130                 135                 140

Ile Ser Gly Val Lys Val Thr Leu Lys Asn Lys Asn Gly Asp Thr Ile
145                 150                 155                 160

Gly Thr Thr Thr Thr Asp Ser Asn Gly Lys Tyr Glu Phe Thr Gly Leu
                    165                 170                 175

Glu Asn Gly Asp Tyr Thr Ile Glu Phe Glu Thr Pro Glu Gly Tyr Thr
                180                 185                 190

Pro Thr Lys Gln Asn Ser Gly Ser Asp Glu Gly Lys Asp Ser Asn Gly
            195                 200                 205

Thr Lys Thr Thr Val Thr Val Lys Asp Ala Asp Asn Lys Thr Ile Asp
210                 215                 220

Ser Gly Phe Tyr Lys Pro Thr Tyr Asn Leu Gly Asp Tyr Val Trp Glu
225                 230                 235                 240

Asp Thr Asn Lys Asp Gly Ile Gln Asp Ser Glu Lys Gly Ile Ser
                245                 250                 255

Gly Val Lys Val Thr Leu Lys Asp Lys Asn Gly Asn Ala Ile Gly Thr
            260                 265                 270

Thr Thr Thr Asp Ala Ser Gly His Tyr Gln Phe Lys Gly Leu Glu Asn
        275                 280                 285

Gly Ser Tyr Thr Val Glu Phe Glu Thr Pro Ser Gly Tyr Thr Pro Thr
    290                 295                 300

Lys Ala Asn Ser Gly Gln Asp Ile Thr Val Asp Ser Asn Gly Ile Thr
305                 310                 315                 320

Thr Thr Gly Ile Ile Asn Gly Ala Asp Asn Leu Thr Ile Asp Ser Gly
                325                 330                 335

Phe Tyr Lys Thr Pro Lys Tyr Ser Val Gly Asp Tyr Val Trp Glu Asp
            340                 345                 350

Thr Asn Lys Asp Gly Ile Gln Asp Asn Glu Lys Gly Ile Ser Gly
                355                 360                 365

Val Lys Val Thr Leu Lys Asp Glu Lys Gly Asn Ile Ile Ser Thr Thr
    370                 375                 380

Thr Thr Asp Glu Asn Gly Lys Tyr Gln Phe Asp Asn Leu Asp Ser Gly
385                 390                 395                 400

Asn Tyr Ile Ile His Phe Glu Lys Pro Glu Gly Met Thr Gln Thr Thr
                405                 410                 415

Ala Asn Ser Gly Asn Asp Asp Glu Lys Asp Ala Asp Gly Glu Asp Val
            420                 425                 430

Arg Val Thr Ile Thr Asp His Asp Asp Phe Ser Ile Asp Asn Gly Tyr
            435                 440                 445

Phe Asp Asp
```

450

<210> SEQ ID NO 4
<211> LENGTH: 452
<212> TYPE: PRT
<213> ORGANISM: Staphylococcus epidermidis

<400> SEQUENCE: 4

```
Pro Thr Tyr Ser Leu Gly Asp Tyr Val Trp Leu Asp Lys Asn Lys Asn
  1               5                  10                  15

Gly Val Gln Asp Asp Glu Lys Gly Leu Ala Gly Val Tyr Val Thr
                 20                  25                  30

Leu Lys Asp Ser Asn Asn Arg Glu Leu Gln Arg Val Thr Thr Asp Gln
             35                  40                  45

Ser Gly His Tyr Gln Phe Asp Asn Leu Gln Asn Gly Thr Tyr Thr Val
         50                  55                  60

Glu Phe Ala Ile Pro Asp Asn Tyr Thr Pro Ser Pro Ala Asn Asn Ser
 65                  70                  75                  80

Thr Asn Asp Ala Ile Asp Ser Asp Gly Glu Arg Asp Gly Thr Arg Lys
                 85                  90                  95

Val Val Val Ala Lys Gly Thr Ile Asn Asn Ala Asp Asn Met Thr Val
            100                 105                 110

Asp Thr Gly Phe Tyr Leu Thr Pro Lys Tyr Asn Val Gly Asp Tyr Val
            115                 120                 125

Trp Glu Asp Thr Asn Lys Asp Gly Ile Gln Asp Asn Glu Lys Gly
            130                 135                 140

Ile Ser Gly Val Lys Val Thr Leu Lys Asn Lys Asn Gly Asp Thr Ile
145                 150                 155                 160

Gly Thr Thr Thr Thr Asp Ser Asn Gly Lys Tyr Glu Phe Thr Gly Leu
                165                 170                 175

Glu Asn Gly Asp Tyr Thr Ile Glu Phe Glu Thr Pro Glu Gly Tyr Thr
            180                 185                 190

Pro Thr Lys Gln Asn Ser Gly Ser Asp Glu Gly Lys Asp Ser Asn Gly
            195                 200                 205

Thr Lys Thr Thr Val Thr Val Lys Asp Thr Asp Asn Lys Thr Ile Asp
        210                 215                 220

Ser Gly Phe Tyr Lys Pro Thr Tyr Asn Leu Gly Asp Tyr Val Trp Glu
225                 230                 235                 240

Asp Thr Asn Lys Asp Gly Ile Gln Asp Ser Glu Lys Gly Ile Ser
                245                 250                 255

Gly Val Lys Val Thr Leu Lys Asp Lys Asn Gly Asn Ala Ile Gly Thr
            260                 265                 270

Thr Thr Thr Asp Ala Ser Gly His Tyr Gln Phe Lys Gly Leu Glu Asn
        275                 280                 285

Gly Ser Tyr Thr Val Glu Phe Glu Thr Pro Ser Gly Tyr Thr Pro Thr
    290                 295                 300

Lys Ala Asn Ser Gly Gln Asp Ile Thr Val Asp Ser Asn Gly Ile Thr
305                 310                 315                 320

Thr Thr Gly Ile Ile Asn Gly Ala Asp Asn Leu Thr Ile Asp Ser Gly
                325                 330                 335

Phe Tyr Lys Thr Pro Lys Tyr Ser Val Gly Asp Tyr Val Trp Glu Asp
            340                 345                 350

Thr Asn Lys Asp Gly Ile Gln Asp Asn Glu Lys Gly Ile Ser Gly
            355                 360                 365

Val Lys Val Thr Leu Lys Asp Glu Lys Gly Asn Ile Ile Ser Thr Thr
```

```
                370                 375                 380
Thr Thr Asp Glu Asn Gly Lys Tyr Gln Phe Asp Asn Leu Asp Ser Gly
385                 390                 395                 400

Asn Tyr Ile Ile His Phe Glu Lys Pro Glu Gly Met Thr Gln Thr Thr
                405                 410                 415

Ala Asn Ser Gly Asn Asp Asp Glu Lys Asp Ala Asp Gly Glu Asp Val
            420                 425                 430

Arg Val Thr Ile Thr Asp His Asp Asp Phe Ser Ile Asp Asn Gly Tyr
            435                 440                 445

Phe Asp Asp Asp
    450

<210> SEQ ID NO 5
<211> LENGTH: 223
<212> TYPE: PRT
<213> ORGANISM: Staphylococcus epidermidis

<400> SEQUENCE: 5

Pro Thr Tyr Asn Leu Gly Asp Tyr Val Trp Glu Asp Thr Asn Lys Asp
1               5                   10                  15

Gly Ile Gln Asp Asp Ser Glu Lys Gly Ile Ser Gly Val Lys Val Thr
            20                  25                  30

Leu Lys Asp Lys Asn Gly Asn Ala Ile Gly Thr Thr Thr Thr Asp Ala
        35                  40                  45

Ser Gly His Tyr Gln Phe Lys Gly Leu Glu Asn Gly Ser Tyr Thr Val
    50                  55                  60

Glu Phe Glu Thr Pro Ser Gly Tyr Thr Pro Thr Lys Ala Asn Ser Gly
65                  70                  75                  80

Gln Asp Ile Thr Val Asp Ser Asn Gly Ile Thr Thr Thr Gly Ile Ile
                85                  90                  95

Asn Gly Ala Asp Asn Leu Thr Ile Asp Ser Gly Phe Tyr Lys Thr Pro
            100                 105                 110

Lys Tyr Ser Val Gly Asp Tyr Val Trp Glu Asp Thr Asn Lys Asp Gly
        115                 120                 125

Ile Gln Asp Asp Asn Glu Lys Gly Ile Ser Gly Val Lys Val Thr Leu
    130                 135                 140

Lys Asp Glu Lys Gly Asn Ile Ile Ser Thr Thr Thr Thr Asp Glu Asn
145                 150                 155                 160

Gly Lys Tyr Gln Phe Asp Asn Leu Asp Ser Gly Asn Tyr Ile Ile His
                165                 170                 175

Phe Glu Lys Pro Glu Gly Met Thr Gln Thr Thr Ala Asn Ser Gly Asn
            180                 185                 190

Asp Asp Glu Lys Asp Ala Asp Gly Glu Asp Val Arg Val Thr Ile Thr
        195                 200                 205

Asp His Asp Asp Phe Ser Ile Asp Asn Gly Tyr Phe Asp Asp
    210                 215                 220

<210> SEQ ID NO 6
<211> LENGTH: 119
<212> TYPE: PRT
<213> ORGANISM: Staphylococcus epidermidis

<400> SEQUENCE: 6

Pro Thr Tyr Ser Leu Gly Asp Tyr Val Trp Leu Asp Lys Asn Lys Asn
1               5                   10                  15

Gly Val Gln Asp Asp Glu Lys Gly Leu Ala Gly Val Tyr Val Thr
            20                  25                  30
```

Leu Lys Asp Ser Asn Asn Arg Glu Leu Gln Arg Val Thr Thr Asp Gln
            35                  40                  45

Ser Gly His Tyr Gln Phe Asp Asn Leu Gln Asn Gly Thr Tyr Thr Val
     50                  55                  60

Glu Phe Ala Ile Pro Asp Asn Tyr Thr Pro Ser Pro Ala Asn Asn Ser
 65                  70                  75                  80

Thr Asn Asp Ala Ile Asp Ser Asp Gly Glu Arg Asp Gly Thr Arg Lys
             85                  90                  95

Val Val Val Ala Lys Gly Thr Ile Asn Asn Ala Asp Asn Met Thr Val
            100                 105                 110

Asp Thr Gly Phe Tyr Leu Thr
            115

<210> SEQ ID NO 7
<211> LENGTH: 110
<212> TYPE: PRT
<213> ORGANISM: Staphylococcus epidermidis

<400> SEQUENCE: 7

Pro Lys Tyr Asn Val Gly Asp Tyr Val Trp Glu Asp Thr Asn Lys Asp
 1               5                  10                  15

Gly Ile Gln Asp Asp Asn Glu Lys Gly Ile Ser Gly Val Lys Val Thr
             20                  25                  30

Leu Lys Asn Lys Asn Gly Asp Thr Ile Gly Thr Thr Thr Thr Asp Ser
            35                  40                  45

Asn Gly Lys Tyr Glu Phe Thr Gly Leu Glu Asn Gly Asp Tyr Thr Ile
     50                  55                  60

Glu Phe Glu Thr Pro Glu Gly Tyr Thr Pro Thr Lys Gln Asn Ser Gly
 65                  70                  75                  80

Ser Asp Glu Gly Lys Asp Ser Asn Gly Thr Lys Thr Thr Val Thr Val
             85                  90                  95

Lys Asp Thr Asp Asn Lys Thr Ile Asp Ser Gly Phe Tyr Lys
            100                 105                 110

<210> SEQ ID NO 8
<211> LENGTH: 111
<212> TYPE: PRT
<213> ORGANISM: Staphylococcus epidermidis

<400> SEQUENCE: 8

Pro Thr Tyr Asn Leu Gly Asp Tyr Val Trp Glu Asp Thr Asn Lys Asp
 1               5                  10                  15

Gly Ile Gln Asp Asp Ser Glu Lys Gly Ile Ser Gly Val Lys Val Thr
             20                  25                  30

Leu Lys Asp Lys Asn Gly Asn Ala Ile Gly Thr Thr Thr Thr Asp Ala
            35                  40                  45

Ser Gly His Tyr Gln Phe Lys Gly Leu Glu Asn Gly Ser Tyr Thr Val
     50                  55                  60

Glu Phe Glu Thr Pro Ser Gly Tyr Thr Pro Thr Lys Ala Asn Ser Gly
 65                  70                  75                  80

Gln Asp Ile Thr Val Asp Ser Asn Gly Ile Thr Thr Thr Gly Ile Ile
             85                  90                  95

Asn Gly Ala Asp Asn Leu Thr Ile Asp Ser Gly Phe Tyr Lys Thr
            100                 105                 110

<210> SEQ ID NO 9
<211> LENGTH: 112

```
<212> TYPE: PRT
<213> ORGANISM: Staphylococcus epidermidis

<400> SEQUENCE: 9

Pro Lys Tyr Ser Val Gly Asp Tyr Val Trp Glu Asp Thr Asn Lys Asp
  1               5                  10                  15

Gly Ile Gln Asp Asp Asn Glu Lys Gly Ile Ser Gly Val Lys Val Thr
             20                  25                  30

Leu Lys Asp Glu Lys Gly Asn Ile Ile Ser Thr Thr Thr Thr Asp Glu
         35                  40                  45

Asn Gly Lys Tyr Gln Phe Asp Asn Leu Asp Ser Gly Asn Tyr Ile Ile
     50                  55                  60

His Phe Glu Lys Pro Glu Gly Met Thr Gln Thr Thr Ala Asn Ser Gly
 65              70                  75                  80

Asn Asp Asp Glu Lys Asp Ala Asp Gly Glu Asp Val Arg Val Thr Ile
                 85                  90                  95

Thr Asp His Asp Asp Phe Ser Ile Asp Asn Gly Tyr Phe Asp Asp Asp
            100                 105                 110

<210> SEQ ID NO 10
<211> LENGTH: 1356
<212> TYPE: DNA
<213> ORGANISM: Staphylococcus epidermidis

<400> SEQUENCE: 10
cctacatata gtctaggtga ctatgtatgg ttagataaaa ataaaaacgg tgttcaagat      60
gatgatgaga aggtttagc aggtgtttat gttactctta agacagtaa caatagagaa      120
ttacaacgtg taactactga tcaatctgga cattatcaat ttgataattt acaaaatgga     180
acgtacacag tcgagtttgc gattcctgat aattatacgc catctcccgc aaataattct     240
acaaatgatg caatagattc agatggtgaa cgtgatggta cacgtaaagt agttgttgcc     300
aaaggaacaa ttaataatgc tgataatatg actgtagata ctggcttta tttaactcct      360
aaatacaatg tcggagatta tgtatgggaa gatacaaata agatggtat ccaagatgac      420
aatgaaaaag gaatttctgg tgttaaagta acgttaaaaa ataaaatgg agatactatt      480
ggcacaacga caacgattc aaatggtaaa tatgaattca ggtttaga gaacggggat        540
tacacaatag aatttgagac gccggaaggc tacacaccga ctaaacaaaa ctcgggaagt     600
gacgaaggta agattcaaa cggtacgaaa acaacagtca cagtcaaaga tacagataat     660
aaaacaatag actcaggttt ctacaagcca acatataact taggtgacta tgtatgggaa     720
gatacaaata agatggtat tcaagacgac agtgaaaaag ggatttctgg ggttaaagtg     780
acgttaaaag ataaaaatgg aaatgccatt gggacaacga caacgacgc aagtggtcat     840
tatcaattta aaggattaga aaatggaagc tacacagttg agtttgagac accatcaggt    900
tatacaccga caaagcgaa ttcaggtcaa gatataactg tagattccaa cggtataaca     960
acaacaggta tcattaacgg agctgataat ctcacaattg atagtggttt ctacaaaaca   1020
ccaaaatata gtgtcggaga ttatgtatgg aagatacaa ataaagatgg tatccaagat    1080
gacaatgaaa agggaatttc tggtgttaaa gtaacgttaa aggatgaaaa aggaaatata   1140
attagcacta caacaactga tgaaaatggg aagtatcaat ttgataattt agatagtggt   1200
aattacatta ttcattttga gaaccggaa ggcatgactc aaactacagc aaattctgga   1260
aatgatgatg aaaagatgc tgatggggaa gatgttcgtg taacgattac tgatcatgat   1320
gactttagta tagataatgg ttattttgac gatgat                             1356
```

```
<210> SEQ ID NO 11
<211> LENGTH: 669
<212> TYPE: DNA
<213> ORGANISM: Staphylococcus epidermidis

<400> SEQUENCE: 11
ccaacatata acttaggtga ctatgtatgg gaagatacaa ataaagatgg tattcaagac     60
gacagtgaaa aagggatttc tggggttaaa gtgacgttaa aagataaaaa tggaaatgcc    120
attgggacaa cgacaacaga cgcaagtggt cattatcaat ttaaaggatt agaaaatgga    180
agctacacag ttgagtttga cacccatca ggttatacac cgacaaaagc gaattcaggt     240
caagatataa ctgtagattc caacggtata acaacaacag gtatcattaa cggagctgat    300
aatctcacaa ttgatagtgg tttctacaaa acaccaaaat atagtgtcgg agattatgta    360
tgggaagata caaataaaga tggtatccaa gatgacaatg aaaagggaat ttctggtgtt    420
aaagtaacgt taaggatga aaaggaaat ataattagca ctacaacaac tgatgaaaat      480
gggaagtatc aatttgataa tttagatagt ggtaattaca ttattcattt tgagaaaccg    540
gaaggcatga ctcaaaactac agcaaattct ggaaatgatg atgaaaaaga tgctgatggg   600
gaagatgttc gtgtaacgat tactgatcat gatgacttta gtatagataa tggttatttt    660
gacgatgat                                                            669

<210> SEQ ID NO 12
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 12
aaaggatccc tggaggtata gtatgaaaaa gag                                   33

<210> SEQ ID NO 13
<211> LENGTH: 45
<212> TYPE: DNA
<213> ORGANISM: Artificial Sequence
<220> FEATURE:
<223> OTHER INFORMATION: A synthetic oligonucleotide

<400> SEQUENCE: 13
aaactgcagc tatttttctt tattatcttt tttacgacgt cttcc                      45

<210> SEQ ID NO 14
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 14
gggccatggc ctacatatag tctaggtgac                                       30

<210> SEQ ID NO 15
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 15
ataccatgga ttatcccct gtgctgttga ag                                     32
```

-continued

<210> SEQ ID NO 16
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 16
attccatggt gagttttcat tatcacgact acc                           33

<210> SEQ ID NO 17
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 17
atagataatg gttatttga cccatggtca gacagtg                        37

<210> SEQ ID NO 18
<211> LENGTH: 35
<212> TYPE: DNA
<213> ORGANISM: Artificial Sequence
<220> FEATURE:
<223> OTHER INFORMATION: A synthetic oligonucleotide

<400> SEQUENCE: 18
aaaggatccg aagacaatca attagaatca gcttc                         35

<210> SEQ ID NO 19
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 19
atactgcaga ttatccccct gtgctgttga ag                            32

<210> SEQ ID NO 20
<211> LENGTH: 30
<212> TYPE: DNA
<213> ORGANISM: Artificial Sequence
<220> FEATURE:
<223> OTHER INFORMATION: A synthetic oligonucleotide

<400> SEQUENCE: 20
gggggatccc ctacatatag tctaggtgac                               30

<210> SEQ ID NO 21
<211> LENGTH: 33
<212> TYPE: DNA
<213> ORGANISM: Artificial Sequence
<220> FEATURE:
<223> OTHER INFORMATION: A synthetic oligonucleotide

<400> SEQUENCE: 21
actctgcaga tcatcgtcaa aataaccatt atc                           33

<210> SEQ ID NO 22
<211> LENGTH: 34
<212> TYPE: DNA
<213> ORGANISM: Artificial Sequence
<220> FEATURE:
<223> OTHER INFORMATION: A synthetic oligonucleotide -continued

```
<400> SEQUENCE: 22
tctggatccg ataacaatat tgagaatatt ggtg                          34

<210> SEQ ID NO 23
<211> LENGTH: 31
<212> TYPE: DNA
<213> ORGANISM: Artificial Sequence
<220> FEATURE:
<223> OTHER INFORMATION: A synthetic oligonucleotide

<400> SEQUENCE: 23
tatctgcagc atatcaatta tgtcctttca c                             31

<210> SEQ ID NO 24
<211> LENGTH: 32
<212> TYPE: DNA
<213> ORGANISM: Artificial Sequence
<220> FEATURE:
<223> OTHER INFORMATION: A synthetic oligonucleotide

<400> SEQUENCE: 24
tatctgcagc ttgtagaaac ctgagtctat tg                            32

<210> SEQ ID NO 25
<211> LENGTH: 37
<212> TYPE: DNA
<213> ORGANISM: Artificial Sequence
<220> FEATURE:
<223> OTHER INFORMATION: A synthetic oligonucleotide

<400> SEQUENCE: 25
tatctgcagt gttttgtaga aaccactatc aattgtg                       37

<210> SEQ ID NO 26
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 26
tatggatccc ctaaatacaa tgtcggagat tatg                          34

<210> SEQ ID NO 27
<211> LENGTH: 34
<212> TYPE: DNA
<213> ORGANISM: Artificial Sequence
<220> FEATURE:
<223> OTHER INFORMATION: A synthetic oligonucleotide

<400> SEQUENCE: 27
ttcggatccc caacatataa cttaggtgac tatg                          34

<210> SEQ ID NO 28
<211> LENGTH: 90
<212> TYPE: DNA
<213> ORGANISM: Staphylococcus epidermidis

<400> SEQUENCE: 28
tggaggtata gtatgaaaaa gagaagacaa ggaccaatta acaagagagt ggattttcta    60
tccaacaagg taaacaagta ctcgattagg                                    90

<210> SEQ ID NO 29
<211> LENGTH: 26
<212> TYPE: PRT
```

```
<213> ORGANISM: Staphylococcus epidermidis

<400> SEQUENCE: 29

Met Lys Lys Arg Arg Gln Gly Pro Ile Asn Lys Arg Val Asp Phe Leu
1               5                   10                  15

Ser Asn Lys Val Asn Lys Tyr Ser Ile Arg
            20                  25

<210> SEQ ID NO 30
<211> LENGTH: 39
<212> TYPE: DNA
<213> ORGANISM: T7 Bacteriophage

<400> SEQUENCE: 30
tctagaaata attttgttta actttaagaa ggagatata                          39

<210> SEQ ID NO 31
<211> LENGTH: 110
<212> TYPE: PRT
<213> ORGANISM: Staphylococcus epidermidis

<400> SEQUENCE: 31

Pro Lys Tyr Asn Val Gly Asp Tyr Val Trp Glu Asp Thr Asn Lys Asp
1               5                   10                  15

Gly Ile Gln Asp Asp Asn Glu Lys Gly Ile Ser Gly Val Lys Val Thr
            20                  25                  30

Leu Lys Asn Lys Asn Gly Asp Thr Ile Gly Thr Thr Thr Thr Asp Ser
        35                  40                  45

Asn Gly Lys Tyr Glu Phe Thr Gly Leu Glu Asn Gly Asp Tyr Thr Ile
    50                  55                  60

Glu Phe Glu Thr Pro Glu Gly Tyr Thr Pro Thr Lys Gln Asn Ser Gly
65                  70                  75                  80

Ser Asp Glu Gly Lys Asp Ser Asn Gly Thr Leu Thr Thr Val Thr Val
                85                  90                  95

Lys Asp Ala Asp Asn Lys Thr Ile Asp Ser Gly Phe Tyr Lys
            100                 105                 110

<210> SEQ ID NO 32
<211> LENGTH: 90
<212> TYPE: DNA
<213> ORGANISM: Staphylococcus epidermidis

<400> SEQUENCE: 32
tggaggtata gtatgaaaaa gagaagacaa ggaccaatta acaagagagt ggattttcta      60
tccaacaagg taaacaagta ctagattagg                                      90

<210> SEQ ID NO 33
<211> LENGTH: 23
<212> TYPE: PRT
<213> ORGANISM: Staphylococcus epidermidis

<400> SEQUENCE: 33

Met Lys Lys Arg Arg Gln Gly Pro Ile Asn Lys Arg Val Asp Phe Leu
1               5                   10                  15

Ser Asn Lys Val Asn Lys Tyr
            20
```

INHIBITING *STAPHYLOCOCCUS EPIDERMIDIS* INFECTIONS

This application claims benefit of the filing date of U.S. Provisional Ser. No. 60/885,098, filed Jan. 16, 2007, the contents of which are specifically incorporated herein by reference in their entirety.

STATEMENT OF GOVERNMENT RIGHTS

The invention was made with the support of a grant from the National Institutes of Health HL077096-02. The United States Government may have certain rights to the invention.

FIELD OF THE INVENTION

The invention relates to compositions useful for inhibiting *Staphylococcus epidermidis* infections, which often infect medical devices. According to the invention, the SdrF protein of *Staphylococcus epidermidis* binds collagen and is involved in surface adherence of *Staphylococcus epidermidis* bacteria to medical devices.

BACKGROUND OF THE INVENTION

Coagulase-negative staphylococci (CNS) are opportunistic pathogens that cause device-related infections such as those in intravascular catheters and ventricular assist devices (VADs). Peters et al. (1982) *J Infect Dis* 146, 479-482; Kristinsson, K. G. (1989) *J Med Microbiol* 28, 249-257; Simon et al. (2005) *Clin Infect Dis* 40, 1108-1115; von Eiff et al., (2002) *Lancet Infect Dis* 2, 677-685; Peters, G. (1988) *J Antimicrob Chemother* 21 Suppl C, 139-148; Heimberger & Duma (1989) *Infectious disease clinics of North America* 3, 221-245; von Eiff et al. (1999) *Infection* 27 Suppl 1, S7-10. *Staphylococcus epidermidis* is the leading cause of these device-related infections accounting for 74 to 92% of the infections caused by CNS. Martin et al. (1989) *Ann Intern Med* 110, 9-16.

The pathogenesis of these infections is complex and involves a wide range of interactions between bacterial and host factors. Therefore, a need exists for further information on the processes by which *Staphylococcus epidermidis* colonizes and infects medical devices and for reagents and methods for preventing such colonization/infection.

SUMMARY OF THE INVENTION

The present invention relates to *Staphylococcus epidermidis* peptides, nucleic acids and antibodies that are useful for inhibiting *Staphylococcus epidermidis* infections and/or colonization of in vivo medical devices.

Thus, one aspect of the invention is isolated *Staphylococcus epidermidis* SdrF peptide comprising SEQ ID NO:3-9, 31 or a combination thereof. In some embodiments, the peptide consists of SEQ ID NO:4, 5, 6, 7, 8, 9, or a combination thereof.

Another aspect of the invention is an isolated nucleic acid encoding the peptide of the invention. In some embodiments, the nucleic acid consists of SEQ ID NO:10 or 11.

Another aspect of the invention is an expression cassette comprising a promoter and a nucleic acid of the invention.

Another aspect of the invention is an expression vector comprising an expression cassette of the invention. Another aspect of the invention is an isolated host cell comprising the nucleic acid of the invention, an expression cassette of the invention or an expression vector of the invention.

Another aspect of the invention is a composition comprising a pharmaceutically acceptable carrier and a peptide of the invention.

Another aspect of the invention is a composition comprising a pharmaceutically acceptable carrier and the nucleic acid of the invention, an expression cassette of the invention or an expression vector of the invention.

Another aspect of the invention is an isolated antibody raised against the peptide of the invention.

Another aspect of the invention is a composition comprising a pharmaceutically acceptable carrier and the antibody of the invention.

Another aspect of the invention is a method of treating or preventing *Staphylococcus epidermidis* infection in a mammal comprising administering to the mammal a composition of the invention. In some embodiments, this method inhibits *Staphylococcus epidermidis* colonization of a medical device in the mammal.

Another aspect of the invention is a method of treating or preventing *Staphylococcus epidermidis* infection in a mammal comprising administering to the mammal a nucleic acid of the invention, an expression cassette of the invention or an expression vector of the invention. In some embodiments, the methods of the invention inhibit *Staphylococcus epidermidis* colonization of a medical device in the mammal.

Another aspect of the invention is a method of treating or preventing *Staphylococcus epidermidis* infection in a mammal comprising administering to the mammal an antibody directed against an SdrF B peptide of the invention. In some embodiments, the methods of the invention inhibit *Staphylococcus epidermidis* colonization of a medical device in the mammal.

DESCRIPTION OF THE FIGURES

FIG. 1A-B illustrate that cells bind to type I collagen when they express SdrF. FIG. 1A shows *S. epidermidis* 9491 cells, which naturally express SdrF, and *L. lactis* NZ9000 harboring the pOri23-SdrF expression vector, both express SdrF on their cell surfaces, as detected by flow cytometry using anti-SdrF antibodies for detection of SdrF. AUF are arbitrary units of fluorescence (percentage of fluorescent events multiplied by the average fluorescence of those events). In contrast, *L. lactis* NZ9000 control cells with the pOri23 vector, which does not encode SdrF, do not express SdrF. FIG. 1B shows that *L. lactis* (pOri-SdrF) and *S. epidermidis* 9491 bind to type I Collagen. AUA are arbitrary units of adherence (number of adherent CFUs per microplate well normalized to each assay's initial inoculum). Data represent the mean plus SEM from at least three separate experiments (two microtiter wells per experiment). The symbol * indicates $p<0.001$ compared with pOri23.

FIG. 2A-B illustrates purification of SdrF ligand binding domains A and B. FIG. 2A is a schematic representation of SdrF as well as the recombinant constructs pQE-rASdrF (encoding ligand binding domain A) and pQE-rBSdrF (encoding ligand binding domain B). The following abbreviations were used: SS, signal sequence. SD, Ser-Asp dipeptide repeat region. W+M, cell wall anchoring and membrane spanning domain. FIG. 2B shows a Coomassie blue stained polyacrylamide gel with electrophoretically separated SdrF domains A and B. Molecular weight markers are shown on the left in kDa.

FIG. 3A-B shows that SdrF mediates *L. lactis* binding to type I collagen via its B ligand binding domain. FIG. 3A is a schematic representation of the *S. epidermidis* DNA regions from the three lactococcal recombinant constructs used in experiments described herein. The following abbreviations were used: P23, lactococcal promoter. SS, signal sequence. SD, Ser-Asp dipeptide repeat region. W+M, cell wall anchoring and membrane spanning domain. FIG. 3B shows bar graphs of SdrF A-related and SdrF B-related fluorescence detected by flow cytometry analysis demonstrating the presence or absence of putative ligand binding domains A and B on the surface of *L. lactis* cells. *L. lactis* cells harbored the following plasmids: pOri23 (*L. lactis* NZ9000 harboring cloning vector pOri23, referred to as "pOri23"); pOri-SdrF (*L. lactis* NZ9000 harboring pOri23 with SdrF; referred to as "SdrF"); pOri-SdrFN8A18 (*L. lactis* NZ9000 harboring pOri-SdrFN8A18, whose insert is depicted in FIG. 3A, referred to as "A18"); and pOri-SdrFN856 (*L. lactis* NZ9000 harboring pOri-SdrFN856, whose insert is depicted in FIG. 3A, referred to as "N856"). AUF are arbitrary units of fluorescence (percentage of fluorescent events multiplied by the average fluorescence of those events). FIG. 3C illustrates binding of *L. lactis* strains (described in FIG. 3B) to type I collagen. AUA are arbitrary units of adherence (number of adherent CFUs per microplate well normalized to each assay's initial inoculum). Data represent the mean and SEM from at least three separate experiments (two microtiter wells per experiment). The symbol * indicates $p<0.01$ compared with pOri23.

FIG. 4A shows that the B domain of SdrF binds to collagen. Interaction of purified recombinant proteins with immobilized type I collagen was assessed by incubation of biotinylated purified truncated polypeptides with collagen-coated wells. Differential biotinylation amongst samples was obviated by expressing adherence as the ratio of A450 between collagen-coated wells vs. BSA-coated wells (A450 Cn/BSA). Irrelevant mature LukS (rLukS) was chosen as a control non-binding polypeptide. The concentration of biotinylated protein employed was 1 µg/ml. The symbol * indicates $p<0.001$ compared with rLukS. FIG. 4B shows that collagen binding increases with increasing concentrations of biotinylated rBSdrF. Increasing concentrations of biotinylated rBSdrF were incubated in BSA-or collagen-coated wells. Nonspecific adherence to BSA wells was subtracted from binding to collagen-coated wells for each concentration (A450 Cn-BSA). Biotinylated adherent protein was detected with streptavidin conjugated with horseradish peroxidase for both FIGS. 4A and 4B. Data represent the mean plus SEM from at least three separate experiments (three microtiter wells per experiment).

FIG. 6A-B shows that antibodies directed against rBSdrF reduce binding of *S. epidermidis* and rBSdrF to type I collagen. FIG. 6A illustrates that purified anti-rBSdrF antibodies reduced the attachment of rBSdrF to collagen in a dose-dependent manner. Purified biotinylated rBSdrF (1 µg/ml) was preincubated with increasing concentrations of either specific anti-rBSdrF (●) or preimmune (■) IgG antibodies before incubation with BSA-or collagen-coated wells. Binding to collagen of rBSdrF after pre-incubation with PBS was considered to be 100% binding. FIG. 6B shows that *S. epidermidis* 9491 bacterial attachment to type I collagen was significantly reduced by anti-rBSdrF IgG antibodies. *S. epidermidis* 9491 cells were preincubated with increasing concentrations of either specific anti-rBSdrF (■) or preimmune (♦) IgGs before incubation in BSA-or collagen-coated wells. Binding of untreated bacterial cells to collagen-coated wells was considered to be 100% binding. Data represent the mean plus SEM from at least three separate experiments (three microtiter wells per experiment). The symbol * indicates that $p<0.05$ compared with control (no IgG antibodies).

FIG. 7A shows an SDS-PAGE gel with electrophoretically separated type I collagen. Following electrophoresis polyacrylamide gel was stained with Coomassie Blue showing a typical band pattern for type I collagen. α1, α2 chains and the β doublet are indicated by arrows. Molecular weights in kDa are indicated to the left. FIG. 7B shows a western blot analysis of binding by recombinant A and B domains of SdrF to electrophoretically separated type I collagen immobilized on PVDF membrane. Immobilized collagen I was incubated with either antibodies against either rASdrF or rBSdrF (control), 40 µg/mL rASdrF followed by antibodies against rASdrF (rASdrF) or 40 µg/mL rBSdrF followed by antibodies against rBSdrF (rBSdrF). Detection was performed using anti-rabbit IgG conjugated to horseradish peroxidase. The α1 chains and the β doublet are indicated by arrows. Molecular weights in kDa are indicated to the right.

FIG. 10 shows a comparison of the SdrF nucleic acid and SdrF amino acid sequences near the beginning of the SdrF genes for the *S. epidermidis* 9491(SEQ ID NO:28 and SEQ ID NO:29) and *S. epidermidis* 9(SEQ ID NO:32 and SEQ ID NO:33) strains of *S. epidermidis*. As shown, the sdrF gene in *S. epidermidis* 9 has a transitional mutation at position 71 (substitution of a cytosine for an adenosine) which creates a stop codon.

Figure 4:
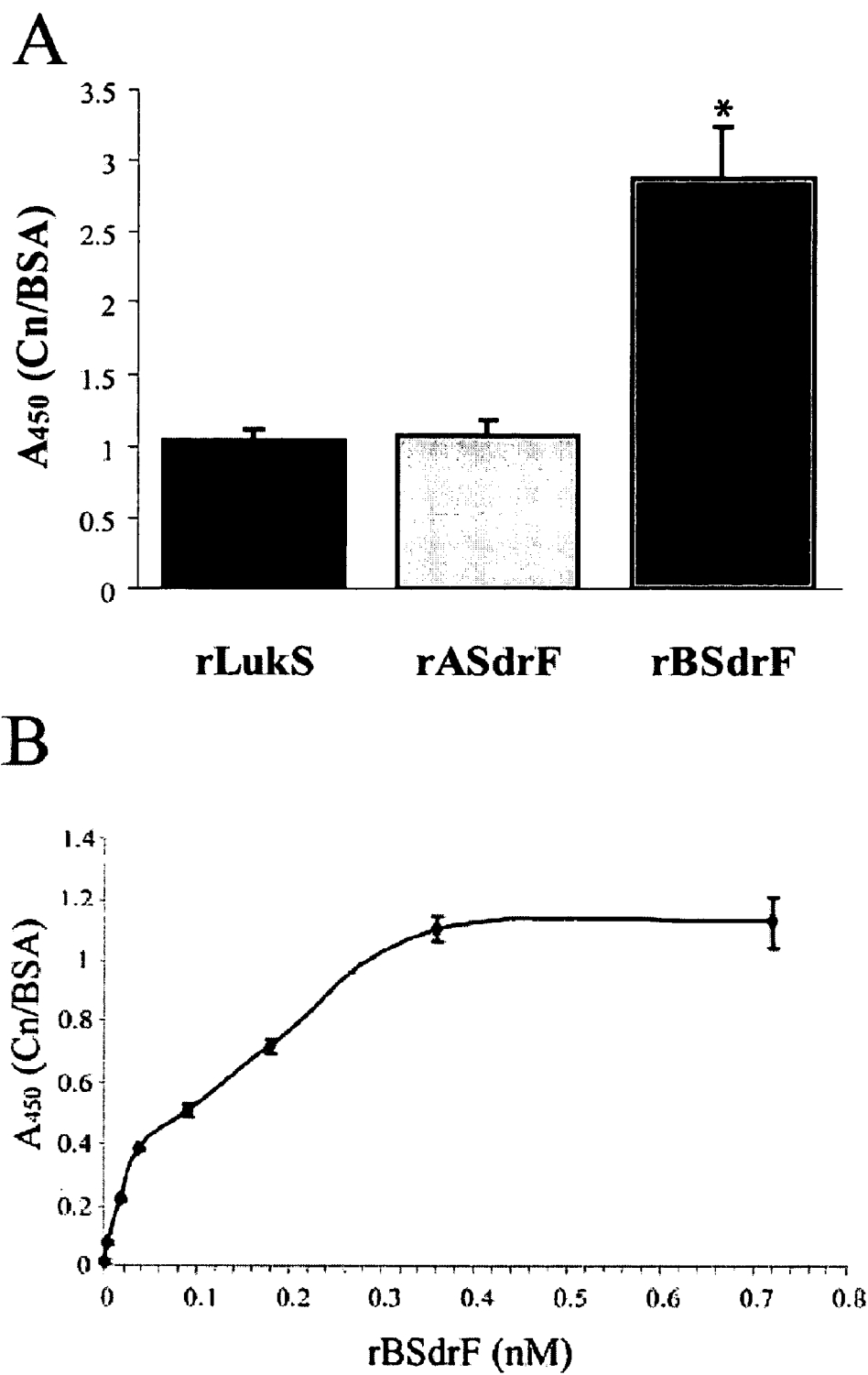
FIG. 4 illustrates binding of purified recombinant SdrF domains (called "rASdrF" and "rBSdrF" domains) to immobilized type I collagen.

*dis* strain 9491, but little or no binding to *S. epidermidis* strain 9 is observed for either of these antibodies.

DETAILED DESCRIPTION OF THE INVENTION

The invention relates to compositions and methods for inhibiting *S. epidermidis* infections. According to the invention, specific peptide sequences in the *S. epidermidis* SdrF protein are responsible for *S. epidermidis* cellular binding to collagen and such binding permits *S. epidermidis* colonization of medical devices, particularly when those medical devices are used in vivo. As illustrated herein, antibodies directed against the *S. epidermidis* peptides responsible for *S. epidermidis* colonization prevent *S. epidermidis* binding to collagen. Also according to the invention, *S. epidermidis* peptides responsible for *S. epidermidis* colonization can also block *S. epidermidis* colonization.

SdrF

Several *S. epidermidis* genes encoding proteins involved in adherence to host factors such as FnG, Fn, Vn or Cn have been described. Some of these proteins have been shown to possess enzymatic properties in addition to their adhesive properties. One of these proteins, the FnG-binding protein serine-aspartate repeat protein G (SdrG), belongs to the serine-aspartate repeat (Sdr) subclass of MSCRAMMs which includes also SdrF and SdrH, whose specific ligands have previously not been identified (Bowden et al., (2005) *Microbiology* (Reading, England) 151, 1453-1464). SdrF and SdrG possess features typical of other MSCRAMMs such as the cell sorting motif LPXTG, a hydrophobic region which spans the bacterial membrane and a carboxyterminal cluster of positively charged residues.

SdrF contains a 52-residue signal sequence followed by a putative ligand-binding domain, termed domain A and another region, domain B. Both of these domains can be subdivided into three and four subdomains respectively. Immediately following the B domain, a 558-residue region composed of repetitive serine-aspartate dipeptides, the SD-repeat region, is present, followed by the LPXTG cell wall-anchoring motif, membrane spanning region and positively charged residues. The SD-repeat region is required for the proper display of the FnG-binding domain of the *Staphylococcus aureus* clumping factor A (ClfA) on the cell surface by spanning through the cell wall and has been suggested to have a similar function in other Sdr proteins (Hartford et al. (1997) *Mol Microbiol* 25, 1065-1076).

According to the present invention, SdrF mediates *S. epidermidis* adherence to transcutaneous drivelines obtained from ventricular assist devices explanted from patients with congestive heart failure. Histological examination of trichrome staining of driveline sections by the inventors indicated that the main host factor coating the subcutaneous part of the driveline was collagen. Data provided herein demonstrate that SdrF binds to collagen type I and the binding is mediated by the B domain.

An example of an amino acid sequence for a strain 9491 *S. epidermidis* cell-surface adhesin SdrF protein can be found in the National Center for Biotechnology Information (NCBI) database (ncbi.nlm.nih.gov/) at accession number AAF72509 (gi: 8101005), and is reproduced below (SEQ ID NO:1).

```
   1 MKKRRQGPIN KRVDFLSNKV NKYSIRKFTV GTASILVGAT
  41 LMFGAADNEA KAAEDNQLES ASKEEQKGSR DNENSKLNQV
  81 DLDNGSHSSE KTTNVNNATE VKKVEAPTTS DVSKPKANEA
 121 VVTNESTKPK TTEAPTVNEE SIAETPKTST TQQDSTEKNN
 161 PSLKDNLNSS STTSKESKTD EHSTKQAQMS TNKSNLDTND
 201 SPTQSEKTSS QANNDSTDNQ SAPSKQLDSK PSEQKVYKTK
 241 FNDEPTQDVE HTTTKLKTPS VSTDSSVNDK QDYTRSAVAS
 281 LGVDSNETEA ITNAVRDNLD LKAASREQIN EAIIAEALKK
 321 DFSNPDYGVD TPLALNRSQS KNSPHKSASP RMNLMSLAAE
 361 PNSGKNVNDK VKITNPTLSL NKSNNHAMNV IWPTSNEQFN
 401 LKANYELDDS IKEGDTFTIK YGQYIRPGGL ELPAIKTQLR
 441 SKDGSIVANG VYDKTTNTTT YTFTNYVDQY QNITGSFDLI
 481 ATPKRETAIK DNQNYPMEVT IANEVVKKDF IVDYGNKKDN
 521 TTTAAVANVD NVNNKHNEVV YLNQNNQNPK YAKYFSTVKN
 561 GEFIPGEVKV YEVTDTNAMV DSFNPDLNSS NVKDVTSQFA
 601 PKVSADGTRV DINFARSMAN GKKYIVTQAV RPTGTGNVYT
 641 EYWLTRDGTT NTNDFYRGTK STTVTYLNGS STAQGDNPTY
 681 SLGDYVWLDK NKNGVQDDDE KGLAGVYVTL KDSNNRELQR
 721 VTTDQSGHYQ FDNLQNGTYT VEFAIPDNYT PSPANNSTND
 761 AIDSDGERDG TRKVVVAKGT INNADNMTVD TGFYLTPKYN
 801 VGDYVWEDTN KDGIQDDNEK GISGVKVTLK NKNGDTIGTT
 841 TTDSNGKYEF TGLENGDYTI EFETPEGYTP TKQNSGSDEG
 881 KDSNGTKTTV TVKDADNKTI DSGFYKPTYN LGDYVWEDTN
 921 KDGIQDDSEK GISGVKVTLK DKNGNAIGTT TTDASGHYQF
 961 KGLENGSYTV EFETPSGYTP TKANSGQDIT VDSNGITTTG
1001 IINGADNLTI DSGFYKTPKY SVGDYVWEDT NKDGIQDDNE
1041 KGISGVKVTL KDEKGNIIST TTTDENGKYQ FDNLDSGNYI
1081 IHFEKPEGMT QTTANSGNDD EKDADGEDVR VTITDHDDFS
1121 IDNGYFDDDS DSDSDADSDS DSDSDSDADS DSDADSDSDA
1161 DSDSDSDSDS DADSDSDSDS DSDSDSDSDA DSDSDSDSDS
1201 DADSDSDSDS DSDSDSDSDS DSDSDSDSDS DSDSDSDSDS
1241 DSDSDADSDS DADSDSDSDS DSDADSDSDS DSDSDADSDS
1281 DSDSDSDSDS DSDADSDSDS DSDSDSDSDS DSDSDSDSDS
1321 DSDADSDSDS DSDSDSDSDS DSDSDSDSDS DSDADSDADS
1361 DSDADSDSDA DSDSDSDSDS DADSDSDSDS DSDSDSDSDS
1401 DSDSDSDSDS DSDSDSDADS DSDSDSDSDS DSDADSDSDS
1441 DSDSDSDADS DSDSDSDSDA DSDSDSDSDS DADSDSDSDS
1481 DSDSDSDSDA DSDSDSDSDS DSDSDSDSDS DSDSDSDSDS
1521 DSDSDSDSDS DSDSDSDSDS DSDSDSDSDS DSDSDSDSDS
1561 DSDSDSDSDS DSDSDSDSDS DSDSDSDSDS DSDSDSDSDS
1601 DSDSDSDSDS DSDSDSDSDS DADSDSDSDS DSDADSDSDS
1641 DSDSDSDSDS DSDSDSDSDS DSDSDSDSDS DSDSDSDSDS
1681 DSDSDSDKNA KDKLPDTGAN EDHDSKGTLL GTLFAGLGAL
```

```
1721  LLGRRRKKDN KEK
```

The SdrF protein has A and B domains. The A domain of SEQ ID NO:1 includes approximately residues 53-677, while the B domain of SEQ ID NO:1 includes approximately residues 678-1128. Thus, the A domain of the SEQ ID NO:1 SdrF protein has the following sequence (SEQ ID NO:2):

```
  53             AEDNQLES ASKEEQKGSR DNENSKLNQV
  81  DLDNGSHSSE KTTNVNNATE VKKVEAPTTS DVSKPKANEA
 121  VVTNESTKPK TTEAPTVNEE SIAETPKTST TQQDSTEKNN
 161  PSLKDNLNSS STTSKESKTD EHSTKQAQMS TNKSNLDTND
 201  SPTQSEKTSS QANNDSTDNQ SAPSKQLDSK PSEQKVYKTK
 241  FNDEPTQDVE HTTTKLKTPS VSTDSSVNDK QDYTRSAVAS
 281  LGVDSNETEA ITNAVRDNLD LKAASREQIN EAIIAEALKK
 321  DFSNPDYGVD TPLALNRSQS KNSPHKSASP RMNLMSLAAE
 361  PNSGKNVNDK VKITNPTLSL NKSNNHANNV IWPTSNEQFN
 401  LKANYELDDS IKEGDTFTIK YGQYIRPGGL ELPAIKTQLR
 441  SKDGSIVANG VYDKTTNTTT YTFTNYVDQY QNITGSFDLI
 481  ATPKRETAIK DNQNYPMEVT IANEVVKKDF IVDYGNKKDN
 521  TTTAAVANVD NVNNKHNEVV YLNQNNQNPK YAKYFSTVKN
 561  GEFIPGEVKV YEVTDTNAMV DSFNPDLNSS NVKDVTSQFA
 601  PKVSADGTRV DINFARSMAN GKKYIVTQAV RPTGTGNVYT
 641  EYWLTRDGTT NTNDFYRGTK STTVTYLNGS STAQGDN
```

Similarly, the B domain of the SEQ ID NO:1 SdrF protein, with amino acids 678-1128, has the following sequence (SEQ ID NO:3):

```
 678                                          PTY
 681  SLGDYVWLDK NKNGVQDDDE KGLAGVYVTL KDSNNRELQR
 721  VTTDQSGHYQ FDNLQNGTYT VEFAIPDNYT PSPANNSTND
 761  AIDSDGERDG TRKVVVAKGT INNADNMTVD TGFYLTPKYN
 801  VGDYVWEDTN KDGIQDDNEK GISGVKVTLK NKNGDTIGTT
 841  TTDSNGKYEF TGLENGDYTI EFETPEGYTP TKQNSGSDEG
 881  KDSNGTKTTV TVKDADNKTI DSGFYKPTYN LGDYVWEDTN
 921  KDGIQDDSEK GISGVKVTLK DKNGNAIGTT TTDASGHYQF
 961  KGLENGSYTV EFETPSGYTP TKANSGQDIT VDSNGITTTG
1001  IINGADNLTI DSGFYKTPKY SVGDYVWEDT NKDGIQDDNE
1041  KGISGVKVTL KDEKGNIIST TTTDENGKYQ FDNLDSGNYI
1081  IHFEKPEGMT QTTANSGNDD EKDADGEDVR VTITDHDDFS
1121  IDNGYFDD
```

The inventors have separately cloned and sequenced a somewhat different SdrF allele. This new SdrF allele encodes an SdrF B domain with the following sequence (SEQ ID NO:4):

```
   1  PTYSLGDYVW LDKNKNGVQD DDEKGLAGVY VTLKDSNNRE
  41  LQRVTTDQSG HYQFDNLQNG TYTVEFAIPD NYTPSPANNS
  81  TNDAIDSDGE RDGTRKVVVA KGTINNADNM TVDTGFYLTP
 121  KYNVGDYVWE DTNKDGIQDD NEKGISGVKV TLKNKNGDTI
 161  GTTTTDSNGK YEFTGLENGD YTIEFETPEG YTPTKQNSGS
 201  DEGKDSNGTK TTVTVKDTDN KTIDSGFYKP TYNLGDYVWE
 241  DTNKDGIQDD SEKGISGVKV TLKDKNGNAI GTTTTDASGH
 281  YQFKGLENGS YTVEFETPSG YTPTKANSGQ DITVDSNGIT
 321  TTGIINGADN LTIDSGFYKT PKYSVGDYVW EDTNKDGIQD
 361  DNEKGISGVK VTLKDEKGNI ISTTTTDENG KYQFDNLDSG
 401  NYIIHFEKPE GMTQTTANSG NDDEKDADGE DVRVTITDHD
 441  DFSIDNGYFD DD
```

The underlined amino acid that is in bold illustrates at least one difference in the amino acid sequence of the SdrF protein identified by the inventors relative to the SdrF sequence SEQ ID NO:1.

The inventors also have identified a small SdrF B peptide that is still capable of binding collagen. This smaller peptide is referred to as the B34 region sequence, and its nucleic acid sequence is provided below (SEQ ID NO:5)

```
 230                                        P TYNLGDYVWE
 241  DTNKDGIQDD SEKGISGVKV TLKDKNGNAI GTTTTDASGH
 281  YQFKGLENGS YTVEFETPSG YTPTKANSGQ DITVDSNGIT
 321  TTGIINGADN LTIDSGFYKT PKYSVGDYVW EDTNKDGIQD
 361  DNEKGISGVK VTLKDEKGNI ISTTTTDENG KYQFDNLDSG
 401  NYIIHFEKPE GMTQTTANSG NDDEKDADGE DVRVTITDHD
 441  DFSIDNGYFD DD
```

The B34 region contains two "B repeats," and according to the invention, one or more B repeats mediate binding of *S. epidermidis* to collagen. The first B repeat identified by the inventors in the SdrF protein includes positions 1 to 119 of the SEQ ID NO:4 SdrF B domain shown above. The sequence of this first B repeat is provided below (SEQ ID NO:6).

```
   1  PTYSLGDYVW LDKNKNGVQD DDEKGLAGVY VTLKDSNNRE
  41  LQRVTTDQSG HYQFDNLQNG TYTVEFAIPD NYTPSPANNS
  81  TNDAIDSDGE RDGTRKVVVA KGTINNADNM TVDTGFYLT
```

A second SdrF B repeat includes 120 to 229 of the SdrF B region identified as SEQ ID NO:4 above. The sequence of this second B repeat is provided below (SEQ ID NO:7).

```
 120                                               P
 121  KYNVGDYVWE DTNKDGIQDD NEKGISGVKV TLKNKNGDTI
 161  GTTTTDSNGK YEFTGLENGD YTIEFETPEG YTPTKQNSGS
 201  DEGKDSNGTK TTVTVKDTDN KTIDSGFYK
```

This second SdrF B repeat can also have an alanine instead of a threonine shown in SEQ ID NO:4 above. The sequence of this second B repeat is provided below (SEQ ID NO:31).

```
120                                                  P
121  KYNVGDYVWE DTNKDGIQDD NEKGISGVKV TLKNKNGDTI
161  GTTTTDSNGK YEFTGLENGD YTIEFETPEG YTPTKQNSGS
201  DEGKDSNGTK TTVTVKDADN KTIDSGFYK
```

A third SdrF B repeat includes positions 230 to 340 of the SdrF B sequence identified as SEQ ID NO:4 above. The sequence of this third B repeat is provided below (SEQ ID NO:8).

```
230                                       P TYNLGDYVWE
241  DTNKDGIQDD SEKGISGVKV TLKDKNGNAI GTTTTDASGH
281  YQFKGLENGS YTVEFETPSG YTPTKANSGQ DITVDSNGIT
321  TTGIINGADN LTIDSGFYKT
```

A fourth SdrF B repeat includes positions 341 to 452 of the SdrF B sequence identified as SEQ ID NO:4 above. The sequence of this fourth B repeat is provided below (SEQ ID NO:9).

```
341                             PKYSVGDYVW EDTNKDGIQD
361  DNEKGISGVK VTLKDEKGNI ISTTTTDENG KYQFDNLDSG
401  NYIIHFEKPE GMTQTTANSG NDDEKDADGE DVRVTITDHD
441  DFSIDNGYFD DD
```

SdrF Mediates Binding of *Staphylococcus epidermidis* to Collagen

*S. epidermidis* adheres to extracellular matrix components such as fibrinogen, fibronectin, vitronectin, laminin and collagen. This ability to adhere to a variety of host components is the major factor that makes *S. epidermidis* an increasingly important nosocomial pathogen and a frequent cause of indwelling device-related infections.

The inventors have recently identified one of these proteins, SdrF, as being involved in bacterial adherence to transcutaneous drivelines from explanted ventricular assist devices. Further examination of the exposed surface of these indwelling devices showed that this binding was to collagen. To overcome the possibility that other *S. epidermidis* proteins might share a common function with SdrF the inventors performed testing with a lactococcal heterologous expression system (Que, Y. A., Haefliger, J. A., Francioli, P., and Moreillon, P. (2000) *Infection and immunity* 68, 3516-3522). Using this approach, the inventors showed that lactococcal cells can bind to type I collagen when the lactococcal cells expressed SdrF.

Using two recombinant *L. lactis* strains, which produced and successfully exported onto their cell surface ligand binding domains A and B, the inventors found that the B domain, but not the A domain, was involved in binding to type I collagen.

Interestingly, it has been recently hypothesized, based on sequence similarity analysis and secondary structure prediction, that the A domain of SdrF would be the most likely candidate to act as the ligand binding domain while the B domain would simply aid in the projection of the A region on the cell surface (Bowden et al., (2005) *Microbiology* (Reading, England) 151, 1453-1464).

The results provided herein, however, demonstrate that the B domain mediates collagen-binding, and that sequences residing within SEQ ID NO:4 and/or 5 mediate such binding.

Also as shown herein, affinity-purified, polyclonal antibodies against SdrF B polypeptides inhibited binding of SdrF B peptides to collagen. The specific anti-SdrF B antibodies caused a profound reduction of purified SdrF B peptide binding to type I collagen even at relatively low concentrations.

Moreover, a similar decrease in binding of *S. epidermidis* 9491 bacterial cells to collagen was detected. This inhibition was very pronounced. Thus, according to the invention, antibodies specific to the SdrF B domain (e.g., SEQ ID NO:4 or 5) can inhibit colonization by *S. epidermidis*.

Anti-SdrF Antibodies Directed Against the SdrF B Region

The invention provides antibody preparations directed against the B region of the *S. epidermidis* B region, for example, antibodies capable of binding a polypeptide having any one of SEQ ID NO:3-9, or a combination thereof. For example, in some embodiments, the antibody can bind a *S. epidermidis* B region epitope that includes SEQ ID NO:4 or 5). The antibody preparations of the invention can serve as inhibitors of *S. epidermidis* infection and/or colonization and therefore act as therapeutic agents.

Methods are provided to prepare and screen for antibodies that preferentially recognize the *S. epidermidis* B region. A peptide sequence (e.g. SEQ ID NO:4 or 5) is used as antigen to raise polyclonal or monoclonal antibodies. The resultant antibodies are selected for binding to the selected peptide sequence, for binding to the *S. epidermidis* B region or for inhibiting *S. epidermidis* infection and/or colonization.

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82, 4592-4596 (1985).

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-2, IgG-3 and IgG-4; IgA-1 and IgA-2. The heavy chains constant domains that correspond to the different classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of the variable domains differ extensively in sequence among antibodies. The variable domains are for binding and determine the specificity of each particular antibody for its particular antigen. However, the variability is not evenly distributed through the variable domains of antibodies. It is concentrated in three segments called complementarity determining regions (CDRs) also known as hypervariable regions both in the light chain and the heavy chain variable domains.

The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal, and is not limited to antibodies that recognize and immunoreact with a specific antigen. In preferred embodiments, in the context of both the therapeutic and screening methods described below, an antibody or fragment thereof is used that is immunospecific for an antigen or epitope of the invention.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called the Fab fragment, each with a single antigen binding site, and a residual "Fc" fragment, so-called for its ability to crystallize readily. Pepsin treatment yields an F(ab')$_2$ fragment that has two antigen binding fragments that are capable of cross-linking antigen, and a residual other fragment (which is termed pFc'). Additional fragments can include diabodies, linear antibodies, single-chain antibody molecules, and multispecific antibodies formed from antibody fragments. As used herein, "functional fragment" with respect to antibodies, refers to Fv, F(ab) and F(ab')$_2$ fragments.

Antibody fragments contemplated by the invention are therefore not full-length antibodies but do have similar or improved immunological properties relative to an anti-*S. epidermidis* B region antibody. Such antibody fragments may be as small as about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids or more. In general, an antibody fragment of the invention can have any upper size limit so long as it binds with specificity to the *S. epidermidis* B region, for example, a peptide having SEQ ID NO:4 or 5.

Antibody fragments retain some ability to selectively bind with its antigen. Some types of antibody fragments are defined as follows:

(1) Fab is the fragment that contains a monovalent antigen-binding fragment of an antibody molecule. A Fab fragment can be produced by digestion of whole antibody with the enzyme papain to yield an intact light chain and a portion of one heavy chain.

(2) Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

(3) (Fab')$_2$ is the fragment of an antibody that can be obtained by treating whole antibody with the enzyme pepsin without subsequent reduction. F(ab')$_2$ is a dimer of two Fab' fragments held together by two disulfide bonds.

(4) Fv is the minimum antibody fragment that contains a complete antigen recognition and binding site. This region consists of a dimer of one heavy and one light chain variable domain in a tight, non-covalent association (VH-VL dimer). It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv including only three CDRs specific for an antigen) has the ability to recognize and bind antigen, although at a lower affinity than the entire binding site.

(5) Single chain antibody ("SCA"), defined as a genetically engineered molecule containing the variable region of the light chain, the variable region of the heavy chain, linked by a suitable polypeptide linker as a genetically fused single chain molecule. Such single chain antibodies are also referred to as "single-chain Fv" or "sFv" antibody fragments. Generally, the Fv polypeptide further includes a polypeptide linker between the VH and VL domains that enables the sFv to form the desired structure for antigen binding. For a review of sFv see Pluckthun in The Pharmacology of Monoclonal Antibodies, vol. 113, Rosenburg and Moore eds. Springer-Verlag, N.Y., pp. 269-315 (1994).

The term "diabodies" refers to a small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161, and Hollinger et al., Proc. Natl. Acad Sci. USA 90: 6444-6448 (1993).

Methods for preparing polyclonal antibodies are available to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference.

Methods for preparing monoclonal antibodies are likewise available to one of skill in the art. See, for example, Kohler & Milstein, Nature, 256:495 (1975); Coligan, et al., sections 2.5.1-2.6.7; and Harlow, et al., in: *Antibodies: A Laboratory Manual*, page 726 (Cold Spring Harbor Pub (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Methods of in vitro and in vivo manipulation of monoclonal antibodies are also available to those skilled in the art. For example, monoclonal antibodies to be used in accordance with the present invention may be made by the hybridoma method first described by Kohler and Milstein, Nature 256, 495 (1975), or may be made by recombinant methods, e.g., as described in U.S. Pat. No. 4,816,567. The monoclonal antibodies for use with the present invention may also be isolated from phage antibody libraries using the techniques described in Clackson et al. Nature 352: 624-628 (1991), as well as in Marks et al., J. Mol Biol. 222: 581-597 (1991). Another method involves humanizing a monoclonal antibody by recombinant means to generate antibodies containing human specific and recognizable sequences. See, for review, Holmes, et al., J. Immunol., 158:2192-2201 (1997) and Vaswani, et al., Annals Allergy, Asthma & Immunol., 81:105-115 (1998).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional polyclonal antibody preparations that typically include different antibodies directed against different determinants (epitopes), each monoclonal antibody is directed against a single determinant on the antigen. In additional to their specificity, the monoclonal antibodies are advantageous in that they are synthesized by the hybridoma culture, uncontaminated by other immunoglobulins. The modifier "monoclonal" indicates that the antibody preparation is a substantially homogeneous population of antibodies, and is not to be construed as requiring production of the antibody by any particular method.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567); Morrison et al. Proc. Natl. Acad Sci. 81, 6851-6855 (1984).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression in *E. coli* of DNA encoding the fragment. Antibody fragments can be obtained by pepsin or papain digestion of whole antibodies conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated in their entireties by reference.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be non-covalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946,778; and Pack, et al., *Bio/Technology* 11:1271-77 (1993).

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The invention contemplates human and humanized forms of non-human (e.g. murine) antibodies. Such humanized antibodies are chimeric immunoglobulins, immunoglobulin chains or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a nonhuman species (donor antibody) such as mouse, rat or rabbit having the desired specificity, affinity and capacity.

In some instances, Fv framework residues of the human immunoglobulin are replaced by corresponding non-human residues. Furthermore, humanized antibodies may comprise residues that are found neither in the recipient antibody nor in the imported CDR or framework sequences. These modifications are made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr. Op. Struct. Biol. 2, 593-596 (1992); Holmes, et al., J. Immunol., 158:2192-2201 (1997) and Vaswani, et al., Annals Allergy, Asthma & Immunol., 81:105-115 (1998).

The invention also provides methods of mutating antibodies to optimize their affinity, selectivity, binding strength or other desirable property. A mutant antibody refers to an amino acid sequence variant of an antibody. In general, one or more of the amino acid residues in the mutant antibody is different from what is present in the reference antibody. Such mutant antibodies necessarily have less than 100% sequence identity or similarity with the reference amino acid sequence. In general, mutant antibodies have at least 75% amino acid sequence identity or similarity with the amino acid sequence of either the heavy or light chain variable domain of the reference antibody. Preferably, mutant antibodies have at least 80%, more preferably at least 85%, even more preferably at least 90%, and most preferably at least 95% amino acid sequence identity or similarity with the amino acid sequence of either the heavy or light chain variable domain of the reference antibody. One method of mutating antibodies involves affinity maturation using phage display.

The invention is therefore directed to a method for selecting antibodies and/or antibody fragments or antibody polypeptides with desirable properties. Such desirable properties can include increased binding affinity or selectivity for the epitopes of the invention The antibodies and antibody fragments of the invention are isolated antibodies and antibody fragments. An isolated antibody is one that has been identified and separated and/or recovered from a component of the environment in which it was produced. Contaminant components of its production environment are materials that would interfere with diagnostic or therapeutic uses for the antibody, and may include enzymes, hormones, and other proteinaceous or nonproteinaceous solutes. The term "isolated antibody" also includes antibodies within recombinant cells because at least one component of the antibody's natural environment will not be present. Ordinarily, however, isolated antibody will be prepared by using at least one purification step If desired, the antibodies of the invention can be purified by any available procedure. For example, the antibodies can be affinity purified by binding an antibody preparation to a solid support to which the antigen used to raise the antibodies is bound. After washing off contaminants, the antibody can be eluted by known procedures. Those of skill in the art will know of various techniques common in the immunology arts for purification and/or concentration of polyclonal antibodies, as well as monoclonal antibodies (see for example, Coligan, et al., Unit 9, *Current Protocols in Immunology*, Wiley Interscience, 1991, incorporated by reference).

In some embodiments, the antibody will be purified as measurable by at least three different methods: 1) to greater than 95% by weight of antibody as determined by the Lowry method, and most preferably more than 99% by weight; 2) to a degree sufficient to obtain at least 15 residues of N-terminal or internal amino acid sequence by use of a spinning cup sequenator; or 3) to homogeneity by SDS-PAGE under reducing or non-reducing conditions using Coomasie blue or, preferably, silver stain.

SdrF B Region Expression Cassettes and Vectors

According to the invention, SdrF B polypeptides can be produced recombinantly and then purified for administration to subjects. In another embodiment, nucleic acids that encode SdrF B can be placed in expression cassettes and/or expression vectors and these SdrF B expression cassettes and expression vectors can also be administered as anti-*S. epidermidis* agents to subjects. Hence, the invention provides SdrF B expression cassettes and SdrF B expression vectors.

SdrF B nucleic acids that can be used in the invention include the following nucleic acid (SEQ ID NO:10):

```
   1  CCTACATATA GTCTAGGTGA CTATGTATGG TTAGATAAAA
  41  ATAAAAACGG TGTTCAAGAT GATGATGAGA AAGGTTTAGC
  81  AGGTGTTTAT GTTACTCTTA AAGACAGTAA CAATAGAGAA
 121  TTACAACGTG TAACTACTGA TCAATCTGGA CATTATCAAT
 161  TTGATAATTT ACAAAATGGA ACGTACACAG TCGAGTTTGC
 201  GATTCCTGAT AATTATACGC CATCTCCCGC AAATAATTCT
 241  ACAAATGATG CAATAGATTC AGATGGTGAA CGTGATGGTA
 281  CACGTAAAGT AGTTGTTGCC AAAGGAACAA TTAATAATGC
 321  TGATAATATG ACTGTAGATA CTGGCTTTTA TTTAACTCCT
 361  AAATACAATG TCGGAGATTA TGTATGGGAA GATACAAATA
 401  AAGATGGTAT CCAAGATGAC AATGAAAAAG GAATTTCTGG
 441  TGTTAAAGTA ACGTTAAAAA ATAAAAATGG AGATACTATT
 481  GGCACAACGA CAACAGATTC AAATGGTAAA TATGAATTCA
 521  CAGGTTTAGA GAACGGGGAT TACACAATAG AATTTGAGAC
 561  GCCGGAAGGC TACACACCGA CTAAACAAAA CTCGGGAAGT
 601  GACGAAGGTA AAGATTCAAA CGGTACGAAA ACAACAGTCA
 641  CAGTCAAAGA TACAGATAAT AAAACAATAG ACTCAGGTTT
 681  CTACAAGCCA ACATATAACT TAGGTGACTA TGTATGGGAA
 721  GATACAAATA AAGATGGTAT TCAAGACGAC AGTGAAAAAG
 761  GGATTTCTGG GGTTAAAGTG ACGTTAAAAG ATAAAAATGG
 801  AAATGCCATT GGGACAACGA CAACAGACGC AAGTGGTCAT
 841  TATCAATTTA AAGGATTAGA AAATGGAAGC TACACAGTTG
 881  AGTTTGAGAC ACCATCAGGT TATACACCGA CAAAAGCGAA
 921  TTCAGGTCAA GATATAACTG TAGATTCCAA CGGTaTAaCA
 961  ACAACAGGTA TCATTAACGG AGCTGATAAT CTCACAATTG
1001  ATAGTGGTTT CTACAAAACA CCAAAATATA GTGTCGGAGA
1041  TTATGTATGG GAAGATACAA ATAAAGATGG TATCCAAGAT
1081  GACAATGAAA AGGGAATTTC TGGTGTTAAA GTAACGTTAA
1121  AGGATGAAAA AGGAAATATA ATTAGCACTA CAACAACTGA
1161  TGAAAATGGG AAGTATCAAT TTGATAATTT AGATAGTGGT
1201  AATTACATTA TTCATTTTGA GAAACCGGAA GGCATGACTC
1241  AAACTACAGC AAATTCTGGA AATGATGATG AAAAAGATGC
1281  TGATGGGGAA GATGTTCGTG TAACGATTAC TGATCATGAT
1321  GACTTTAGTA TAGATAATGG TTATTTTGAC GATGAT
```

Alternatively, a smaller nucleic acid can be used that encodes a portion of the SdrF B region that the inventors have shown is still capable of binding collagen. This smaller peptide is referred to as the B34 region sequence, and its nucleic acid sequence is provided below (SEQ ID NO:11):

```
  1  CCAACATATA ACTTAGGTGA CTATGTATGG GAAGATACAA
 41  ATAAAGATGG TATTCAAGAC GACAGTGAAA AAGGGATTTC
 81  TGGGGTTAAA GTGACGTTAA AAGATAAAAA TGGAAATGCC
121  ATTGGGACAA CGACAACAGA CGCAAGTGGT CATTATCAAT
161  TTAAAGGATT AGAAAATGGA AGCTACACAG TTGAGTTTGA
201  GACACCATCA GGTTATACAC CGACAAAAGC GAATTCAGGT
241  CAAGATATAA CTGTAGATTC CAACGGTaTA aCAACAACAG
281  GTATCATTAA CGGAGCTGAT AATCTCACAA TTGATAGTGG
321  TTTCTACAAA ACACCAAAAT ATAGTGTCGG AGATTATGTA
361  TGGGAAGATA CAAATAAAGA TGGTATCCAA GATGACAATG
401  AAAAGGGAAT TTCTGGTGTT AAAGTAACGT TAAAGGATGA
441  AAAAGGAAAT ATAATTAGCA CTACAACAAC TGATGAAAAT
481  GGGAAGTATC AATTTGATAA TTTAGATAGT GGTAATTACA
521  TTATTCATTT TGAGAAACCG GAAGGCATGA CTCAAACTAC
561  AGCAAATTCT GGAAATGATG ATGAAAAAGA TGCTGATGGG
601  GAAGATGTTC GTGTAACGAT TACTGATCAT GATGACTTTA
641  GTATAGATAA TGGTTATTTT GACGATGAT
```

SdrF B nucleic acids can be placed within linear or circular molecules. They can be placed within autonomously replicating molecules or within molecules without replication sequences. They can be regulated by their own or by other regulatory sequences, as is known in the art. Nucleic acid constructs encoding SdrF B may include transcriptional regulatory elements, such as a promoter element, an enhancer or UAS element, and a transcriptional terminator signal, for controlling transcription of the SdrF B sequences in the cells.

The expression cassettes of the invention include a promoter. Any promoter able to direct transcription of an encoded peptide or polypeptide may be used. Accordingly, many promoters may be included within the expression cassette of the invention. Some useful promoters include constitutive promoters, inducible promoters, regulated promoters, cell specific promoters, viral promoters, and synthetic promoters. A promoter is a nucleotide sequence that controls expression of an operably linked nucleic acid sequence by providing a recognition site for RNA polymerase, and possibly other factors, required for proper transcription. A promoter includes a minimal promoter, consisting only of all basal elements needed for transcription initiation, such as a TATA-box and/or other sequences that serve to specify the site of transcription initiation. A promoter may be obtained from a variety of different sources. For example, a promoter may be derived entirely from a native gene, be composed of different elements derived from different promoters found in nature, or be composed of nucleic acid sequences that are entirely synthetic. A promoter may be derived from many different types of organisms and tailored for use within a given cell.

For expression of a polypeptide in a bacterium, an expression cassette having a bacterial promoter will be used. A bacterial promoter is any DNA sequence capable of binding bacterial RNA polymerase and initiating the downstream (3") transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an operator may be present and overlap an adjacent RNA polymerase binding site at which RNA synthesis begins. The operator permits negatively regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *E. coli* (Raibaud et al., *Ann. Rev. Genet.*, 18:173 (1984)). Regulated expression may therefore be positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (Chang et al., *Nature*, 198:1056 (1977), and maltose. Additional examples include promoter sequences derived from biosynthetic enzymes such as tryptophan (Trp) (Goeddel et al., *Nuc. Acids Res.*, 8:4057 (1980); Yelverton et al., *Nuc. Acids Res.*, 9:731 (1981); U.S. Pat. No. 4,738,921; and EPO Publ. Nos. 036 776 and 121 775). The β-lactamase (bla) promoter system (Weissmann, "The cloning of interferon and other mistakes", in: Interferon 3 (ed. I. Gresser), 1981), and bacteriophage lambda $P_L$ (Shimatake et al., *Nature*, 292:128 (1981)) and T5 (U.S. Pat. No. 4,689,406) promoter systems also provide useful promoter sequences. A preferred promoter is the *Chlorella* virus promoter (U.S. Pat. No. 6,316,224).

Synthetic promoters that do not occur in nature also function as bacterial promoters. For example, transcription activation sequences of one bacterial or bacteriophage promoter may be joined with the operon sequences of another bacterial or bacteriophage promoter, creating a synthetic hybrid promoter (U.S. Pat. No. 4,551,433). For example, the tac promoter is a hybrid trp-lac promoter comprised of both trp promoter and lac operon sequences that is regulated by the lac repressor (Amann et al., *Gene*, 25:167 (1983); de Boer et al., *Proc. Natl. Acad. Sci. USA*, 80:21 (1983)). Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system (Studier et al., *J. Mol. Biol.*, 189:113 (1986); Tabor et al., *Proc. Natl. Acad. Sci. USA*, 82:1074 (1985)). In addition, a hybrid promoter can also be comprised of a bacteriophage promoter and an *E. coli* operator region (EPO Publ. No. 267 851).

An expression cassette having a baculovirus promoter can be used for expression of a polypeptide in an insect cell. A baculovirus promoter is any DNA sequence capable of binding a baculovirus RNA polymerase and initiating transcription of a coding sequence into mRNA. A promoter will have a transcription initiation region that is usually placed proximal to the 5' end of the coding sequence. This transcription initiation region usually includes an RNA polymerase binding site and a transcription initiation site. A second domain called an enhancer may be present and is usually distal to the structural gene. A baculovirus promoter may be a regulated promoter or a constitutive promoter. Useful promoter sequences may be obtained from structural genes that are transcribed at times late in a viral infection cycle. Examples include sequences derived from the gene encoding the baculoviral polyhedron protein (Friesen et al., "The Regulation of Baculovirus Gene Expression", in: The Molecular Biology of Baculoviruses (ed. Walter Doerfler), 1986; and EPO Publ. Nos. 127 839 and 155 476) and the gene encoding the baculoviral p10 protein (Vlak et al., *J. Gen. Virol.*, 69:765 (1988)).

Promoters that are functional in yeast are known to those of ordinary skill in the art. In addition to an RNA polymerase binding site and a transcription initiation site, a yeast promoter may also have a second region called an upstream activator sequence. The upstream activator sequence permits regulated expression that may be induced. Constitutive expression occurs in the absence of an upstream activator sequence. Regulated expression may be either positive or negative, thereby either enhancing or reducing transcription.

Promoters for use in yeast may be obtained from yeast genes that encode enzymes active in metabolic pathways. Examples of such genes include alcohol dehydrogenase (ADH) (EPO Publ. No. 284 044), enolase, glucokinase, glucose-6-phosphate isomerase, glyceraldehyde-3-phosphatedehydrogenase (GAP or GAPDH), hexokinase, phosphofructokinase, 3-phosphoglyceratemutase, and pyruvate kinase (PyK). (EPO Publ. No. 329 203). The yeast PHO5 gene, encoding acid phosphatase, also provides useful promoter sequences. (Myanohara et al., *Proc. Natl. Acad. Sci. USA*, 80:1 (1983)).

Synthetic promoters that do not occur in nature may also be used for expression in yeast. For example, upstream activator sequences from one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876, 197 and 4,880,734). Other examples of hybrid promoters include promoters which consist of the regulatory sequences of either the ADH2, GAL4, GAL10, or PHO5 genes, combined with the transcriptional activation region of a glycolytic enzyme gene such as GAP or PyK (EPO Publ. No. 164 556). Furthermore, a yeast promoter can include naturally occurring promoters of non-yeast origin that have the ability to bind yeast RNA polymerase and initiate transcription. Examples of such promoters are known in the art. (Cohen et al., *Proc. Natl. Acad. Sci. USA*, 77:1078 (1980); Henikoff et al., *Nature*, 283:835 (1981); Hollenberg et al., *Curr. Topics Microbiol. Immunol.*, 96:119 (1981)); Hollenberg et al., "The Expression of Bacterial Antibiotic Resistance Genes in the Yeast *Saccharomyces cerevisiae*", in: Plasmids of Medical, Environmental and Commercial Importance (eds. K. N. Timmis and A. Puhler), 1979; (Mercerau-Puigalon et al., *Gene*, 11:163 (1980); Panthier et al., *Curr. Genet.*, 2:109 (1980)).

Many mammalian promoters are known in the art that may be used in conjunction with the expression cassette of the invention. Mammalian promoters often have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter may also contain an upstream promoter element, usually located within 100 to 200 bp upstream of the TATA box. An upstream promoter element determines the rate at which transcription is initiated and can act in either orientation (Sambrook et al., "Expression of Cloned Genes in Mammalian Cells", in: Molecular Cloning: A Laboratory Manual, 2nd ed., 1989).

Mammalian viral genes are often highly expressed and have a broad host range; therefore sequences encoding mammalian viral genes often provide useful promoter sequences. Examples include the SV40 early promoter, mouse mammary tumour virus LTR promoter, adenovirus major late promoter (Ad MLP), and herpes simplex virus promoter. In addition, sequences derived from non-viral genes, such as the murine metallothionein gene, also provide useful promoter sequences. Expression may be either constitutive or regulated.

A mammalian promoter may also be associated with an enhancer. The presence of an enhancer will usually increase transcription from an associated promoter. An enhancer is a regulatory DNA sequence that can stimulate transcription up to 1000-fold when linked to homologous or heterologous promoters, with synthesis beginning at the normal RNA start site. Enhancers are active when they are placed upstream or downstream from the transcription initiation site, in either normal or flipped orientation, or at a distance of more than 1000 nucleotides from the promoter. (Maniatis et al., *Science*, 236:1237 (1987)); Alberts et al., Molecular Biology of the Cell, 2nd ed., 1989). Enhancer elements derived from viruses are often times useful, because they usually have a broad host range. Examples include the SV40 early gene enhancer (Dijkema et al., *EMBO J.*, 4:761 (1985)) and the enhancer/promoters derived from the long terminal repeat (LTR) of the Rous Sarcoma Virus (Gorman et al., *Proc. Natl. Acad. Sci. USA*, 79:6777 (1982b)) and from human cytomegalovirus (Boshart et al., *Cell*, 41:521 (1985)). Additionally, some enhancers are regulatable and become active only in the presence of an inducer, such as a hormone or metal ion (Sassone-Corsi and Borelli, *Trends Genet.*, 2:215 (1986); Maniatis et al., *Science*, 236:1237 (1987)).

It is understood that many promoters and associated regulatory elements may be used within the expression cassette of the invention to transcribe an encoded polypeptide. The promoters described above are provided merely as examples and are not to be considered as a complete list of promoters that are included within the scope of the invention.

The expression cassette of the invention may contain a nucleic acid sequence for increasing the translation efficiency of an mRNA encoding a polypeptide of the invention. Such increased translation serves to increase production of the polypeptide. The presence of an efficient ribosome binding site is useful for gene expression in prokaryotes. In bacterial mRNA, a conserved stretch of six nucleotides, the Shine-Dalgarno sequence, is usually found upstream of the initiating AUG codon. (Shine et al., *Nature*, 254:34 (1975)). This sequence is thought to promote ribosome binding to the mRNA by base pairing between the ribosome binding site and the 3' end of *Escherichia coli* 16S rRNA. (Steitz et al., "Genetic signals and nucleotide sequences in messenger RNA", in: Biological Regulation and Development: Gene Expression (ed. R. F. Goldberger), 1979)). Such a ribosome binding site, or operable derivatives thereof, are included within the expression cassette of the invention.

A translation initiation sequence can be derived from any expressed *Escherichia coli* gene and can be used within an expression cassette of the invention. Preferably the gene is a highly expressed gene. A translation initiation sequence can be obtained via standard recombinant methods, synthetic techniques, purification techniques, or combinations thereof, which are all well known. (Ausubel et al., *Current Protocols in Molecular Biology*, Green Publishing Associates and Wiley Interscience, NY. (1989); Beaucage and Caruthers, *Tetra. Letts.*, 22:1859 (1981); VanDevanter et al., *Nucleic Acids Res.*, 12:6159 (1984). Alternatively, translational start sequences can be obtained from numerous commercial vendors. (Operon Technologies; Life Technologies Inc, Gaithersburg, Md.). In some embodiments, the T7 translation initiation sequence is used. The T7 translation initiation sequence is derived from the highly expressed T7 Gene 10 cistron and can have a sequence that includes TCTAGAAATAATTTTGTTTAACTTT AAGAAGGAGATATA (SEQ ID NO:30). Other examples of translation initiation sequences include, but are not limited to, the maltose-binding protein (Mal E gene) start sequence (Guan et al., *Gene*, 67:21 (1997)) present in the pMalc2 expression vector (New England Biolabs, Beverly, Mass.) and the translation initiation sequence for the following genes: thioredoxin gene (Novagen, Madison, Wis.), Glutathione-S-transferase gene (Pharmacia, Piscataway, N.J.), β-galactosidase gene, chloramphenicol acetyltransferase gene and *E. coli* Trp E gene (Ausubel et al., 1989, *Current Protocols in Molecular Biology*, Chapter 16, Green Publishing Associates and Wiley Interscience, NY).

Eucaryotic mRNA does not contain a Shine-Dalgarno sequence. Instead, the selection of the translational start codon is usually determined by its proximity to the cap at the 5' end of an mRNA. The nucleotides immediately surrounding the start codon in eucaryotic mRNA influence the efficiency of translation. Accordingly, one skilled in the art can determine what nucleic acid sequences will increase translation of a polypeptide encoded by the expression cassette of the invention. Such nucleic acid sequences are within the scope of the invention.

The invention therefore provides an expression cassette that includes a promoter operable in a selected host and a nucleic acid encoding an SdrF B peptide, for example, having SEQ ID NO:4 or 5. The expression cassette can have other elements, for example, a start codon, a stop codon, transcription termination signals, origins of replication, enhancers, and the like as described herein. The expression cassette can also be placed in a vector for easy replication and maintenance.

SdrF B nucleic acids can also be placed in expression cassettes or gene delivery vehicles for the purpose of delivering a SdrF B nucleic acids to a site in a mammalian body, e.g., a site where SdrF b peptides can be expressed and stimulate an immune response or a site where *S. epidermidis* infection or colonization may occur. According to the present invention, a delivery vehicle can be, for example, naked plasmid DNA, a viral expression vector, or a SdrF B nucleic acid of the invention in conjunction with a liposome or a condensing agent.

In addition, *Lactococcus lactis* host cells can be used as an immunogen, particularly when these bacterial cells have been engineered to express surface proteins. Accordingly, the invention is also drawn to recombinant *Lactococcus lactis* host cells that contain an expression cassette of the invention and/or that express any of the present SdrF peptides. Such recombinant SdrF can be used in an immunological composition or vaccine for controlling or inhibiting *Staphylococcus epidermidis* infection in a mammal.

Methods of Use

Peptides of the invention can be employed to prevent, treat or otherwise ameliorate infection by a *S. epidermidis*. In one embodiment, the invention provides a method for preventing, treating or otherwise ameliorating acute or chronic infection, by *S. epidermidis*, of a mammal such as a human. In another embodiment, the invention provides a method for preventing, treating or otherwise ameliorating acute or chronic infection, by *S. epidermidis*, of a medical device in a mammal such as a human.

As used herein "preventing" is intended to include the administration of a peptide of the invention to a mammal such as a human who could be or has been exposed to *S. epidermidis*. The mammal who could be exposed to *S. epidermidis*, includes without limitation, someone who may have an internal medical device, for example, a ventricular assist device.

*S epidermidis* are well adapted to adhere to smooth metal and plastic surfaces of foreign bodies, such as vascular catheters, cardiac devices, and ventricular catheters. Therefore, this is a major pathogen in central nervous system infections with cerebrospinal fluid (CSF) shunts, in phlebitis and bacteremia associated with intravenous catheters, in endocarditis following cardiac surgery, in skeletal infections in patients who have orthopedic devices, and in peritonitis associated with peritoneal dialysis catheters.

Treatment of, or treating a *S. epidermidis* infection is intended to include a reduction of the bacterial growth rate, reduction of detectable bacterial cells or the alleviation of or diminishment of at least one symptom typically associated with the infection. The treatment also includes alleviation or diminishment of more than one symptom. Ideally, the treatment cures, e.g., substantially inhibits infection and/or eliminates the symptoms associated with the infection.

Methods of preventing, treating or otherwise ameliorating acute or chronic infection include administering to a mammal such as a human a therapeutically effective amount of a peptide or a nucleic acid of the present invention. In general, if a nucleic acid is administered, the nucleic acid construct should include sequences for expression of a SdrF B peptide encoded by the nucleic acid. Alternatively, antibodies directed against SdrF B peptides (e.g., peptides with SEQ ID NO:4 or 5) can be administered to the mammal having, in danger of having or suspected of having a *Staphylococcus epidermidis* infection.

Dosages, Formulations and Routes of Administration

One aspect of the invention is a composition comprising a carrier and one or more of the SdrF peptides or SdrF nucleic acids of the invention. Another aspect of the invention is a composition comprising a carrier and an antibody raised against one or more of the SdrF peptides of the invention.

The compositions of the invention are administered so as to ameliorate one or more symptoms of *Staphylococcus epidermidis* infection. In some embodiments, the compositions of the invention are administered so as to achieve a reduction in *Staphylococcus epidermidis* colonization of medical devices.

To achieve the desired effect(s), the therapeutic agent or the combination of therapeutic agents, may be administered as single or divided dosages, for example, of at least about 0.01 mg/kg to about 500 to 750 mg/kg, of at least about 0.01 mg/kg to about 300 to 500 mg/kg, at least about 0.1 mg/kg to about 100 to 300 mg/kg or at least about 1 mg/kg to about 50 to 100 mg/kg of body weight, although other dosages may provide beneficial results. The amount administered will vary depending on various factors including, but not limited to, what types of therapeutic agents are administered, the route of administration, the progression or lack of progression of the disease (e.g. *Staphylococcus epidermidis* infection and/or colonization), the weight, the physical condition, the health, the age of the patient, whether prevention or treatment is to be achieved, and if the peptides or antibodies are chemically modified. Such factors can be readily determined by the clinician employing animal models or other test systems that are available in the art.

The therapeutic agents may be administered in a single dose, in multiple doses, in a continuous or intermittent manner, depending, for example, upon the recipient's physiological condition, whether the purpose of the administration is therapeutic or prophylactic, and other factors known to skilled practitioners. These therapeutic agents may be administered essentially continuously over a pre-selected period of time or may be administered in a series of spaced doses. Both local and systemic administration is contemplated.

To prepare the composition, the therapeutic agents are synthesized or otherwise obtained, and purified as necessary or desired. These therapeutic agents can then be lyophilized or stabilized, their concentrations can be adjusted to an appropriate amount, and these therapeutic agents can optionally be combined with other agents.

In general, dosage forms of the invention comprise an amount of at least one of the agents of the invention effective to treat or prevent the clinical symptoms of a disease (e.g. *Staphylococcus epidermidis* infection and/or colonization). Any statistically significant attenuation of one or more symptoms of *Staphylococcus epidermidis* infection is considered to be a treatment of *Staphylococcus epidermidis* infection. The absolute weight of a therapeutic agent or combination thereof that is included in a unit dose can vary widely. For example, about 0.01 to about 2 g, or about 0.1 to about 500 mg, of at least one therapeutic agent can be administered. Alternatively, the unit dosage can vary from about 0.01 g to about 50 g, from about 0.01 g to about 35 g, from about 0.1 g to about 25 g, from about 0.5 g to about 12 g, from about 0.5 g to about 8 g, from about 0.5 g to about 4 g, or from about 0.5 g to about 2 g.

Daily doses of a therapeutic agent can vary as well. Such daily doses can range, for example, from about 0.1 g/day to about 50 g/day, from about 0.1 g/day to about 25 g/day, from about 0.1 g/day to about 12 g/day, from about 0.5 g/day to about 8 g/day, from about 0.5 g/day to about 4 g/day, and from about 0.5 g/day to about 2 g/day.

Thus, one or more suitable unit dosage forms comprising the therapeutic agents of the invention can be administered by a variety of routes including oral, parenteral (including subcutaneous, intravenous, intramuscular and intraperitoneal), rectal, dermal, transdermal, intrathoracic, intrapulmonary and intranasal (respiratory) routes.

In some embodiments, medical devices are coated with or incubated in one or more of the therapeutic agents of the invention. For example, the peptides of the invention mediate binding between *Staphylococcus epidermidis* and collagen. By incubating a medical device in a peptide of the invention any site that might otherwise have served as a "foothold" for *Staphylococcus epidermidis* colonization becomes saturated with the present *Staphylococcus epidermidis* peptides. Once coated with the present peptides, the medical devices will resist colonization by *Staphylococcus epidermidis*.

The therapeutic agents may also be formulated for immediate or sustained release in an animal to treat, prevent or inhibit *Staphylococcus epidermidis* infection. For example, microencapsulation can be used to prepare a sustained release formation (see WO 94/07529, and U.S. Pat. No. 4,962,091).

The formulations may, where appropriate, be conveniently presented in discrete unit dosage forms and may be prepared by any of the methods well known to the pharmaceutical arts. Such methods may include the step of mixing the therapeutic agent with liquid solutions, solid matrices, semi-solid pharmaceutical carriers, finely divided solid pharmaceutical carriers or combinations thereof, and then, if necessary, introducing or shaping the product into the desired delivery system.

When the therapeutic agents of the invention are prepared for oral administration, they are generally combined with a pharmaceutically acceptable carrier, diluent or excipient to form a pharmaceutical formulation, or unit dosage form. For oral administration, the therapeutic agents may be present as a powder, a granular formulation, a solution, a suspension, an emulsion or in a natural or synthetic polymer or resin for ingestion of the active ingredients from a chewing gum. The therapeutic agents may also be presented as a bolus, electuary or paste. Orally administered therapeutic agents of the invention can also be formulated for sustained release. For example, the therapeutic agents can be coated, micro-encapsulated, or otherwise placed within a sustained delivery device. The total active ingredients in such formulations comprise from 0.1 to 99.9% by weight of the formulation.

By "pharmaceutically acceptable" it is meant a pharmaceutical carrier, diluent, excipient, and/or salt that is compatible with the other ingredients of the formulation, and not deleterious to the recipient thereof. A "pharmaceutically acceptable carrier" or a "pharmaceutical carrier" is a non-active ingredient that is not deleterious to the recipient thereof and that can solubilize or disperse the active ingredients to facilitate formulation of a convenient dosage form.

Pharmaceutical formulations containing the therapeutic agents of the invention can be prepared by procedures known in the art using well-known and readily available ingredients. For example, the therapeutic agent can be formulated with common excipients, diluents, or carriers, and formed into tablets, capsules, solutions, suspensions, powders, aerosols and the like. Examples of excipients, diluents, and carriers that are suitable for such formulations include buffers, as well as fillers and extenders such as starch, cellulose, sugars, mannitol, and silicic derivatives. Binding agents can also be included such as carboxymethyl cellulose, hydroxymethylcellulose, hydroxypropyl methylcellulose and other cellulose derivatives, alginates, gelatin, and polyvinyl-pyrrolidone. Moisturizing agents can be included such as glycerol, disintegrating agents such as calcium carbonate and sodium bicarbonate. Agents for retarding dissolution can also be included such as paraffin. Resorption accelerators such as quaternary ammonium compounds can also be included. Surface active agents such as cetyl alcohol and glycerol monostearate can be included. Adsorptive pharmaceutical carriers such as kaolin and bentonite can be added. Lubricants such as talc, calcium and magnesium stearate, and solid polyethylene glycols can also be included. Preservatives may also be added. The compositions of the invention can also contain thickening agents such as cellulose and/or cellulose derivatives. They may also contain gums such as xanthan, guar or carbo gum or gum arabic, or alternatively polyethylene glycols, bentones and montmorillonites, and the like.

For example, tablets or caplets containing the therapeutic agents of the invention can include buffering agents such as calcium carbonate, magnesium oxide and magnesium carbonate. Caplets and tablets can also include inactive ingredients such as cellulose, pre-gelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, zinc stearate, and the like. Hard or soft gelatin capsules containing at least one therapeutic agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric-coated caplets or tablets containing one or more of the therapeutic agents of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous, intraperitoneal or intravenous routes. The pharmaceutical formulations of the therapeutic agents of the invention can also take the form of an aqueous or anhydrous solution or dispersion, or alternatively the form of an emulsion or suspension or salve.

Thus, the therapeutic agents may be formulated for parenteral administration (e.g., by injection, for example, bolus injection or continuous infusion) and may be presented in unit dose form in ampoules, pre-filled syringes, small volume infusion containers or in multi-dose containers. As noted above, preservatives can be added to help maintain the shelve life of the dosage form. The active agents and other ingredients may form suspensions, solutions, or emulsions in oily or aqueous vehicles, and may contain formulatory agents such as suspending, stabilizing and/or dispersing agents. Alternatively, the therapeutic agents and other ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable carriers, vehicles and adjuvants that are well known in the art. It is possible, for example, to prepare solutions using one or more aqueous or organic solvent(s) that is/are acceptable from the physiological standpoint, chosen, in addition to water, from solvents such as acetone, ethanol, isopropyl alcohol, glycol ethers such as the products sold under the name "Dowanol," polyglycols and polyethylene glycols, $C_1$-$C_4$ alkyl esters of short-chain acids, ethyl or isopropyl lactate, fatty acid triglycerides such as the products marketed under the name "Miglyol," isopropyl myristate, animal, mineral and vegetable oils and polysiloxanes.

One of skill in the art may also add antioxidants, surfactants, other preservatives, film-forming, keratolytic or comedolytic agents, perfumes, flavorings and colorings. Antioxidants such as t-butylhydroquinone, butylated hydroxyanisole, butylated hydroxytoluene and α-tocopherol and its derivatives can be added.

Additionally, the therapeutic agents are well suited to formulation as sustained release dosage forms and the like. The formulations can be so constituted that they release the active agent, for example, in a particular part of the vascular system or respiratory tract, possibly over a period of time. Coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, draining devices and the like.

For topical administration, the therapeutic agents may be formulated as is known in the art for direct application to a target area. Forms chiefly conditioned for topical application take the form, for example, of creams, milks, gels, dispersion or microemulsions, lotions thickened to a greater or lesser extent, impregnated pads, ointments or sticks, aerosol formulations (e.g., sprays or foams), soaps, detergents, lotions or cakes of soap. Other conventional forms for this purpose include wound dressings, coated bandages or other polymer coverings, ointments, creams, lotions, pastes, jellies, sprays, and aerosols. Thus, the therapeutic agents of the invention can be delivered via patches or bandages for dermal administration. Alternatively, the therapeutic agents can be formulated to be part of an adhesive polymer, such as polyacrylate or acrylate/vinyl acetate copolymer. For long-term applications it might be desirable to use microporous and/or breathable backing laminates, so hydration or maceration of the skin can be minimized. The backing layer can be any appropriate thickness that will provide the desired protective and support functions. A suitable thickness will generally be from about 10 to about 200 microns.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1-85% by weight.

Drops, such as eye drops or nose drops, may be formulated with one or more of the therapeutic agents in an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid pharmaceutical carrier.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the pharmaceutical carriers and/or diluents that are useful in the pharmaceutical formulations of the present invention include water and physiologically acceptable buffered saline solutions such as phosphate buffered saline solutions pH 7.0-8.0.

The active ingredients of the invention can also be administered to the respiratory tract. Thus, the present invention also provides aerosol pharmaceutical formulations and dosage forms for use in the methods of the invention.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatin or blister packs from which the powder may be administered with the aid of an inhalator, insufflator, or a metered-dose inhaler (see, for example, the pressurized metered dose inhaler (MDI) and the dry powder inhaler disclosed in Newman, S. P. in *Aerosols and the Lung*, Clarke, S. W. and Davia, D. eds., pp. 197-224, Butterworths, London, England, 1984).

Therapeutic agents of the present invention can also be administered in an aqueous solution when administered in an aerosol or inhaled form. Thus, other aerosol pharmaceutical formulations may comprise, for example, a physiologically acceptable buffered saline solution containing between about 0.1 mg/ml and about 100 mg/ml of one or more of the therapeutic agents of the present invention specific for the indication or disease to be treated. Dry aerosol in the form of finely divided solid therapeutic agent that are not dissolved or suspended in a liquid are also useful in the practice of the present invention. Therapeutic agents of the present invention may be formulated as dusting powders and comprise finely divided particles having an average particle size of between about 1 and 5 µm, alternatively between 2 and 3 µm. Finely divided particles may be prepared by pulverization and screen filtration using techniques well known in the art. The particles may be administered by inhaling a predetermined quantity of the finely divided material, which can be in the form of a powder.

It will be appreciated that the unit content of active ingredient or ingredients contained in an individual aerosol dose of each dosage form need not in itself constitute an effective amount for treating the particular immune response, cancer or other disease since the necessary effective amount can be reached by administration of a plurality of dosage units. Moreover, the effective amount may be achieved using less than the dose in the dosage form, either individually, or in a series of administrations.

For administration to the upper (nasal) or lower respiratory tract by inhalation, the therapeutic agents of the invention are conveniently delivered from a nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Nebulizers include, but are not limited to, those described in U.S. Pat. Nos. 4,624,251; 3,703,173; 3,561,444; and 4,635,627. Aerosol delivery systems of the type disclosed herein are available from numerous commercial sources including Fisons Corporation (Bedford, Mass.), Schering Corp. (Kenilworth, N.J.) and American Pharmoseal Co., (Valencia, Calif.). For intra-nasal administration, the therapeutic agent may also be administered via nose drops, a liquid spray, such as via a plastic bottle atomizer or metered-dose inhaler. Typical of atomizers are the Mistometer (Wintrop) and the Medihaler (Riker).

Furthermore, the active ingredients may also be used in combination with other therapeutic agents, for example, pain relievers, anti-inflammatory agents, anti-bacterial agents and the like, whether for the conditions described or some other condition.

Kits

The present invention further pertains to a packaged composition such as a kit or other container for inhibiting S. epidermidis infection. In one embodiment, the kit or container holds a composition comprising an S. epidermidis peptide of the invention. In another embodiment, the kit or container includes an antibody that binds to S. epidermidis or an S. epidermidis peptide of the invention. In a further embodiment, the kit or container includes a nucleic acid that encodes a SdrF B peptide of the invention.

The kits of the invention can also comprise containers with tools useful for administering the compositions of the invention. Such tools include syringes, swabs, catheters, antiseptic solutions and the like.

The following Examples further illustrate the invention and are not intended to be limiting thereof.

EXAMPLE 1

Experimental Procedures

The abbreviations used are: CNS, coagulase negative staphylococci; VADs, ventricular assist devices; MSCRAMMs, microbial components recognizing adhesive matrix molecules; FnG, fibrinogen; Fn, fibronectin; Vn, vitronectin; Cn, collagen; Sdr, serine-aspartate repeat; PBS, phosphate buffered saline; BSA, bovine serum albumin.

Bacterial Strains and Growth Conditions. *Escherichia coli* XL1-Blue or XL10-Gold (Stratagene) were used as the first recipient strains in routine DNA cloning according to the manufacturer's instructions. *S. aureus* RN4220 (Kreiswirth et al., (1983) *Nature* 305, 709-712) was used as the first Gram-positive host strain for receiving chimeric plasmids originated in *E. coli* before their transfer into their final host. *S. epidermidis* 9491 has been described previously (McCrea et al., (2000) *Microbiology* (Reading, England) 146, 1535-1546). *Lactococcus lactis* NZ9000 (Kuipers et al. (1998) *J. Biotechnol.* 64, 15-21) was used as the host strain for cell surface expression of recombinant *S. epidermidis* proteins. *E. coli* was grown at 37° C. in Luria Bertani broth (BD Biosciences). *S. aureus* was grown in Tryptic Soy broth (BD Biosciences) at 37° C. *S. epidermidis* was grown at 37° C. in Tryptic Soy broth supplemented with 0.25% glucose. *L. lactis* was grown in M17 broth (BD Biosciences) supplemented with 0.5% glucose (GM17) at 30° C. Mannitol Salt Agar was routinely used as solid media for *S. epidermidis*. Other solid media consisted of the corresponding liquid media supplemented with 1.1% Agar. Ampicillin (Ap) (100 µg/ml), erythromycin (Em) (500 µg/ml for *E. coli* strains; 5 µg/ml for *L. lactis* strains) were incorporated to the medium when appropriate.

DNA Constructions. Routine DNA manipulations were performed by standard methods (Sambrook et al. (1989) *Molecular Cloning A Laboratory Manual*, Second edition Ed., Cold Spring Harbor Laboratory Press, Cold Spring Harbor). Plasmid DNA was isolated using QIAprep Spin Miniprep Kit (Qiagen) according to the manufacturer's instructions. Buffer P1 was supplemented with mutanolysin (100 U/ml) and lysozyme (100 µg/ml) for *L. lactis* plasmid DNA isolation and with lysostaphin (50 µg/ml) for *S. aureus* plasmid DNA isolation.

PCR products and DNA fragments embedded in agarose gels were purified using QIAquick PCR Purification Kit and QIAquick Gel Extraction Kit (Qiagen), respectively. PCR was performed using Platinum PCR High Fidelity Supermix (Invitrogen) according to manufacturer's instructions. All recombinant plasmid inserts were sequenced to ensure no errors had been introduced during PCR amplification.

Plasmids created during this study are shown in Table 1.

TABLE 1

| | | Plasmids | | |
|---|---|---|---|---|
| Name | Vector | Insert | Oligonucleotides used | Features |
| pOri-SdrF | pOri23 | Full length sdrF | SDRF-5Bam, SDRF-3Pst | *L. lactis* cell surface expression |

TABLE 1-continued

Plasmids

| Name | Vector | Insert | Oligonucleotides used | Features |
|---|---|---|---|---|
| pOri-SdrFN8 | pOri23 | Full length sdrF plus NcoI site | SDRF-5Bam, SDRF-A3Nco SDRF-A5Nco, SDRF-3Pst | *L. lactis* cell surface expression |
| pOri-SdrFNA18 | pOri23 | sdrF lacking region A | SDRF-5Bam, F-SS + A1Nco | *L. lactis* cell surface expression |
| pOri-SdrFN856 | pOri23 | sdrF lacking region B | F-R5Nco, SDRF-3Pst | *L. lactis* cell surface expression |
| pQE-rASdrF | pQE-30 | Region A of sdrF | F-HisA5Bam, F-HisA3Pst | Amino-terminal His Tag |
| pQE-rBSdrF | pQE-30 | Region B of sdrF | F-HisB5Bam, F-HisB3Pst | Amino-terminal His Tag |
| pQE-lukS | pQE-30 | lukS-PV | lukS-5Bam, lukS-3Pst | Amino-terminal His Tag |
| pQE-rB12 | pQE-30 | B1 and B2 Repeats of sdrF | F-HisB5Bam, QEB2-3Pst | Amino-terminal His Tag |
| pQE-rB123 | pQE-30 | B1, B2 and B3 Repeats of sdrF | F-HisB5Bam, QEB3-3Pst | Amino-terminal His Tag |
| pQE-rB23 | pQE-30 | B2 and B3 Repeats of sdrF | QEB2-5Bam, QEB3-3Pst | Amino-terminal His Tag |
| pQE-rB234 | pQE-30 | B2, B3 and B4 Repeats of sdrF | QEB2-5Bam, F-HisB3Pst | Amino-terminal His Tag |

Oligonucleotides were designed to allow amplification by PCR of the appropriate DNA fragments generating specific restriction sites on both ends of the fragment (Table 2).

TABLE 2

Oligonucleotide Primers

| Name | Sequence (5'-3')a | Endonuclease |
|---|---|---|
| SDRF-5Bam SEQ ID NO: 12 | AAAGGATCCCTGGAGGTATAGTATGAA AAAGAG | BamHI |
| SDRF-3Pst SEQ ID NO: 13 | AAACTGCAGCTATTTTTCTTTATTATC TTTTTTACGACGTCTTCC | PstI |
| SDRF-A5Nco SEQ ID NO: 14 | GGGCCATGGCCTACATATAGTCTAGGT GAC | NcoI |
| SDRF-A3Nco SEQ ID NO: 15 | ATACCATGGATTATCCCCCTGTGCTGT TGAAG | NcoI |
| F-SS + A1Nco SEQ ID NO: 16 | ATTCCATGGTGAGTTTTCATTATCACG ACTACC | NcoI |
| F-R5Nco SEQ ID NO: 17 | ATAGATAATGGTTATTTTGACCCATGG TCAGACAGTG | NcoI |
| F-HisA5Bam SEQ ID NO: 18 | AAAGGATCCGAAGACAATCAATTAGAA TCAGCTTC | BamHI |
| F-HisA3Pst SEQ ID NO: 19 | ATACTGCAGATTATCCCCCTGTGCTGT TGAAG | PstI |
| F-HisB5Bam SEQ ID NO: 20 | GGGGGATCCCCTACATATAGTCTAGGT GAC | BamHI |
| F-HisB3Pst SEQ ID NO: 21 | ACTCTGCAGATCATCGTCAAAATAACC ATTATC | PstI |
| lukS-5Bam SEQ ID NO: 22 | TCTGGATCCGATAACAATATTGAGAAT ATTGGTG | BamHI |
| lukS-3Pst SEQ ID NO: 23 | TATCTGCAGCATATCAATTATGTCCTT TCAC | PstI |
| QEB2-3Pst SEQ ID NO: 24 | TATCTGCAGCTTGTAGAAACCTGAGTC TATTG | PstI |
| QEB3-3Pst SEQ ID NO: 25 | TATCTGCAGTGTTTTGTAGAAACCACT ATCAATTGTG | PstI |
| QEB2-5Bam SEQ ID NO: 26 | TATGGATCCCCTAAATACAATGTCGGA GATTATG | BamHI |
| QEB3-5Bam SEQ ID NO: 27 | TTCGGATCCCCAACATATAACTTAGGT GACTATG | BamHI |

The full length sdrF coding region as well as truncated versions lacking either the A (SEQ ID NO:2) or B (SEQ ID NO:3) domains were used to generate polypeptides for experimentation. These sdrF nucleic acids were cloned into plasmid pOri23 (Que et al., (2000) Infection and Immunity 68: 3516-22). Such DNA fragments were subsequently digested with the suitable restriction endonucleases (New England Biolabs) and ligated to pOri23 previously digested with the same pair of restriction endonucleases. The full length A and B regions of sdrF as well as the region encoding the mature LukS-PV polypeptide from *S. aureus* (Prevost et al. *Infect. Immun.* 63, 4121-4129 (1995)) were, in the same way, amplified by PCR, digested and ligated to pQE-30 (Qiagen).

Transformation of *S. aureus* and *L. lactis*. *L. lactis*. NZ9000 and *S. aureus* RN4220 were transformed as described in Schenk, S., and Laddaga, R. A. (1992) *FEMS microbiology letters* 73, 133-138 and Wells, J. M., Wilson, P. W., and Le Page, R. W. (1993) *J Appl Bacteriol* 74, 629-636.

Expression and Purification of Histidine-Tagged Recombinant Proteins. For the expression of recombinant LukS-PV (rLukS) and SdrF truncated polypeptides, pQE-30 derived recombinant plasmids (Table 1) were cloned into *E. coli* XL1-Blue. Overnight cultures were inoculated into fresh medium and grown to an A600 of 0.3. Isopropyl β-D-thiogalactopyranoside was added to a concentration of 1 mM and the culture was further grown for 4 h. Cells were harvested by centrifugation, resuspended in phosphate-buffered saline (PBS) supplemented with protease inhibitor (Roche Applied Science), imidazole (20 mM) and lysozyme (500 µg/ml) and incubated on ice for 30 min. Cells were lysed by sonication (Branson Ultrasonics) and cell debris was removed by centrifugation. Recombinant proteins expressed, containing an amino-terminal polyhistidine fusion, were purified using HiTrap™ Chelating HP columns (GE Healthcare) according to the manufacturer's instructions and dialyzed extensively against PBS. Protein concentrations were determined using Bio-Rad Protein Assay (Bio-Rad).

Polyclonal Antibodies Preparation and Purification. Polyclonal antibodies were produced at Covance Research Products Inc. by immunization of New Zealand White rabbits with purified recombinant A or B domains of SdrF (rASdrF or rBSdrF) using methods described in Andreola et al. (2004) *J Biol Chem* 279, 3434-3438. Total IgGs from antisera directed against rASdrF (anti-rASdrF) and rBSdrF (anti-rBSdrF) were purified using ImmunoPure® (A) IgG Purification Kit (Pierce Biotechnology) according to the manufacturer's instructions. Specific IgGs were further purified by affinity chromatography with MicroLink Protein Coupling Kit (Pierce Biotechnology) according to the manufacturer's instructions.

Solid Phase Assay of Bacterial Adherence. Microtiter plates (MaxiSorp, Nalge Nunc International) were coated with 5 µg of type I Collagen (Sigma) in 100 µl of PBS per well overnight at 4° C. Wells were washed three times with PBS, blocked with 2% (w/v) non-fat dry milk (Bio-Rad) in PBS for 1 h and washed 5 times with PBS. Log-phase *S. epidermidis* or *L. lactis* cultures were centrifuged, bacterial cells were resuspended in PBS, adjusted to an $OD_{600}$ of 1 or 0.5, respectively, and added to the microtiter wells. After 1 h at 37° C., wells were extensively washed with PBS and the adherent bacteria were collected using two sequential incubations with Trypsin/EDTA 1× (Invitrogen). Bacterial cell suspensions were serially diluted, plated onto the appropriate solid culture media and quantified after 24 h. Adherence to type I collagen was obtained for each sample by subtracting the number of adherent CFUs in milk-coated wells from those lifted from Collagen-coated wells. To measure the competition of Cn binding between *S. epidermidis* and purified proteins, blocked microtiter wells were preincubated with 80 µl of solutions at different protein concentrations for 90 min at room temperature. *S. epidermidis* cell suspensions were adjusted to an $OD_{600}$ of 5, then 20 µl of cells was added to each microtiter well, and incubation, washing, and collection of bacteria were carried out as mentioned above.

Labeling of Recombinant Proteins. Purified recombinant proteins were labeled with EZLink® NHS-LC-Biotin (Pierce) according to the manufacturer's instructions.

Solid Phase Assay of Protein-Protein Interactions. The interactions between type I Collagen and different truncated forms of SdrF were tested using a protocol described by Bowden et al. ((2002) *J Biol Chem* 277, 43017-43023) with modifications. Briefly, microtiter plates (MaxiSorp, Nalge Nunc International) were coated in a similar manner as described for the assay for bacterial adherence studies, blocked with 2% (w/v) bovine serum albumin (BSA) in PBS for 1 h and different amounts of biotinylated purified recombinant proteins (1 µg/ml unless otherwise indicated) were added. Following 2 h of incubation at room temperature, wells were washed with PBS containing 0.05% (v/v) of Tween 20 (PBST) and subsequently incubated for 45 min with ImmunoPure® Streptavidin, Horseradish Peroxidase Conjugated (Pierce Biotechnology) in blocking solution (0.1 µg/ml). Wells were then extensively washed with PBST and development was performed using 1-Step™ Ultra TMB-ELISA (Pierce Biotechnology) according to the manufacturer's instructions. Absorbance at 450 nm ($A_{450}$) was measured using a Bio-Rad 680 Microplate Reader (Bio-Rad).

SDS-PAGE and Western Blot. Sodium dodecyl sulfate-polyacrylamide gel electrophoresis (SDSPAGE) and Western Blots were performed by standard procedures using Immobilon™-P transfer membrane (Millipore). Cell wall-associated proteins were extracted from *L. lactis* and *S. epidermidis* as described by Que et al. ((2000) *Infection and immunity* 68, 3516-3522).

Western Ligand Blot. Samples were dissolved in Laemmli Sample Buffer (Bio-Rad), either boiled or incubated at 37° C. for 10 min, subjected to SDS-PAGE through a 10% polyacrylamide gel and transferred onto Immobilon™-P membrane (Millipore) using a Trans-blot® SD Semi-dry Transfer Cell (Bio-Rad). Membrane was blocked with 5% (w/v) non-fat dry milk in PBST, washed three times with PBST, incubated for 2 h at room temperature with the appropriate purified recombinant protein in PBS (10 µg/ml) and washed three times with PBS. The membrane was then incubated overnight at 4° C. with the corresponding purified rabbit IgG, washed three times with PBST followed by incubation for 1 h with anti-rabbit IgG peroxidase antibodies (Sigma) and three washes with PBST. Visualization was carried out with ECL™ Western Blotting Detection Reagents (GE Healthcare).

Collagen Type I Fractionation. Collagen I α1 and α2 polypeptide chains were separated and purified as described by Acil et al. (*J. Chromatogr. A* 758, 313-318 (1997)).

Flow Cytometry. Bacterial cells were harvested by centrifugation and resuspended in PBS. Approximately $10^8$ CFUs were incubated for 30 min with either anti-rASdrF or anti-rBSdrF IgGs, washed once with PBS, similarly incubated with anti-rabbit IgG conjugated to fluorescein isothiocyanate (FITC) (Sigma), washed with PBS and resuspended in 1 mL of PBS. Cytometric analysis was performed in a FACScan cell analyzer (BD Biosciences) using CellQuest PRO software.

Statistical Analysis. All data from protein-protein interaction assays and bacterial adherence assays represent the mean±standard error (S.E.) of at least three different experiments using triplicate wells for each condition tested. Statistical analysis was performed by pair wise comparisons with Student's t Test.

EXAMPLE 2

SdrF Peptides Mediate Binding of *Staphylococcus epidermidis* to Collagen

This Example illustrates that *Staphylococcus epidermidis* binds collagen through the SdrF polypeptide.

Presence of SdrF on the Cell Surface of *L. lactis* Elicits Adherence to Type I Collagen. The inventors have recently found that SdrF from *S. epidermidis* mediated adhesion to patient-explanted ventricular assist device drivelines when expressed and exported onto the lactococcal cell surface. Similarly it was observed that the major component of the layer of host components that coat such implanted materials was collagen. Therefore, to determine whether cell surface expressed SdrF can bind collagen a heterologous lactococcal expression system was first used to clone the full length sdrF gene from *S. epidermidis* 9491 into the shuttle vector pOri23.

Constitutive expression of sdrF and successful export of SdrF onto the lactococcal cell surface was then assessed by whole cell FITC-labeling and flow cytometry analysis using both anti-rASdrF and anti-rBSdrF IgGs (FIG. 1A). Adherence to immobilized solid-phase type I Collagen was therefore tested. As previously reported, *S. epidermidis* 9491 bound type I Collagen (FIG. 1B) and *L. lactis* cells expressing SdrF on its surface were also able to bind type I Collagen at a significantly higher level than *L. lactis* control cells containing only cloning vector pOri23 (FIG. 1B). *L. lactis* pOri-SdrF cells showed better binding capacity compared with *S. epidermidis* 9491, which may be explained by an increase in the presence of SdrF on the lactococcal cell surface as indicated by flow cytometry analysis. This, in turn, could be due to either increased protein expression or better presentation of SdrF antigens on the cell surface.

Expression and Purification of rASdrF and rBSdrF from *S. epidermidis*. SdrF is composed of two putative ligand-binding regions (Bowden et al., (2005) *Microbiology* (Reading, England) 151, 1453-1464; McCrea et al. (2000) *Microbiology* (Reading, England) 146, 1535-1546). To further characterize the Collagen binding activity of SdrF, recombinant forms of these two regions, A and B (residues 53-677 and 678-1128, respectively) were cloned and expressed in *E. coli* with a N-terminal His tag (FIG. 2A). These polypeptides, with predicted molecular masses of 70 kDa for rASdrF and 51 kDa for rBSdrF, were subsequently purified by metal chelate affinity chromatography and dialyzed against PBS. Purity was confirmed by SDS-PAGE analysis (FIG. 2B). Both fusion proteins migrated with higher apparent molecular masses. Aberrant migration in SDS-PAGE has previously been observed in other *S. aureus* and *S. epidermidis* MSCRAMMs and might be due to their hydrophilic nature (McCrea et al., (2000) *Microbiology* (Reading, England) 146, 1535-1546; Ni Eidhin et al. (1998) *Mol Microbiol* 30, 245-257; Davis et al.(2001) *J Biol Chem* 276, 27799-27805). These two purified polypeptides were used as antigens for the production of rabbit polyclonal antibodies.

The B Domain of SdrF Mediates the Adherence of *L. lactis* to Type I Collagen. To further analyze the SdrF mechanism of binding to Collagen a series of *L. lactis* strains harboring recombinant plasmids were created that expressed different truncated forms of the SdrF polypeptide (Table 1). First, an NcoI restriction site was introduced between the A and B coding regions by DNA ligation of two PCR products comprising both ends of the full length sdrF gene to pOri23 (Table 2) (FIG. 3A) thus obtaining plasmid pOri-SdrFN8. This plasmid was subsequently digested with either BamHI and NcoI, or NcoI and PstI, purified and ligated to the appropriate PCR product (Table 2) previously digested with the same pair of restriction enzymes (FIG. 3A). The plasmids constructed in this manner, pOri-SdrFNA18 and pOri-SdrFN856, were then introduced in *L. lactis* NZ9000 for recombinant protein expression. Interestingly, it was found that introducing the DNA fragment containing just the sdrF signal sequence ligated to the B domain invariably yielded one or more mutations in this fragment (data not shown). Therefore the DNA fragment containing the sdrF signal sequence had to be extended to include the first 22 codons of the A domain (FIG. 3A). Successful protein export and anchor to the lactococcal cell wall was demonstrated by flow cytometry analysis of whole cells using the total IgG fractions purified from polyclonal antisera obtained by immunization of rabbits with purified rASdrF and rBSdrF (anti-rASdrF total IgGs and anti-rBSdrF total IgGs, respectively) (FIG. 3B). Flow cytometry showed an apparent increase in recombinant protein presence on the cell surface of A18 cells compared with SdrF cells (FIG. 3B). However, immunoblot analysis of cell wall-associated proteins showed similar levels of full-length SdrF and its truncated forms (data not shown). These results may be due to a better accessibility to the B domain by anti-rBSdrF antibodies in cell surface-bound recombinant proteins lacking the N-terminal A domain. In view of the immunoblots results and the potential for better accessibility to the B domain by anti-rBSdrF antibodies, it appears that the relative levels of both SdrF-truncated forms are similar to that of the full-length SdrF polypeptide.

Once the presence of cell surface recombinant proteins had been demonstrated, Collagen-binding levels were assessed for these *L. lactis* strains. It was thus observed that NZ9000 cells harboring pOri-SdrFNA 18 (B domain) were able to bind to collagen-coated wells with a significantly higher affinity than control NZ9000 cells containing pOri23 (FIG. 3C). On the other hand, presence of the plasmid pOri-SdrFN856 (A domain) in *L. lactis* cells did not significantly increase their ability to adhere to immobilized type I Collagen (FIG. 3C).

Cells expressing the full length SdrF protein seemed to show a higher level of binding to type I Collagen than those containing a truncated form lacking the A domain on their cell surface although the difference is not statistically significant (FIG. 3C). Taken together, these results suggest that the B domain is the main SdrF component involved in adherence to type I Collagen while the A domain does not mediate any adherence to Collagen.

Recombinant Domain B, but not Domain A, Binds to Type I Collagen. The possibility that another region or regions in the mature truncated form of SdrF expressed by pOri-SdrFNA18 might also contribute to Collagen-binding led to further analysis of this protein-protein interaction using a different approach. The collagen binding activities of the recombinant rASdrF and rBSdrF domains were assessed using a solid-phase assay in which Collagen-coated wells were incubated with either biotin-labeled SdrF putative ligand-binding domain and detected in an ELISA-type manner.

For this purpose LukS-PV, an *S. aureus* leukocidin, was chosen as a negative control protein for absence of adherence to type I Collagen in the subsequent series of solid-phase assays. The DNA encoding the mature LukS-PV polypeptide was therefore cloned, expressed, purified and biotinylated (Tables 1 and 2). Significant differential biotinylation among some of the different preparations of purified biotinylated recombinant proteins was observed, both among different proteins and among different preparations of the same biotinylated protein. This inherent variability was accounted for by expressing binding levels as the ratio between the $A_{450}$ in Cn-versus BSA-coated wells (Cn/BSA). Results demonstrated that rBSdrF caused a significant difference in Cn/BSA with respect to rLukS, whereas rASdrF did not cause any significant binding to type I Cn (FIG. 4A).

To further characterize this interaction between rBSdrF and solid-phase type I Collagen different concentrations of the biotinylated protein were tested. The results show that rBSdrF adheres to type I Collagen in a concentration-dependent saturable manner (FIG. 4B). In this ligand-receptor interaction assay maximum binding occurs at about 20 ng/mL of rBSdrF.

Single B Repeats Can Mediate Collagen I Binding. The B domain of SdrF is composed of four repetitive amino acid sequences termed B repeats. These repeats are 119, 110, 111, and 111 residues long and have on average 55% identity at the amino acid level with each other. To further analyze the mechanism of binding of rBSdrF to type I Collagen, all four B repeats were independently cloned and the corresponding poly-histidine tagged peptides were purified. These polypeptides were then biotinylated and tested for Collagen binding.

Figure 5:
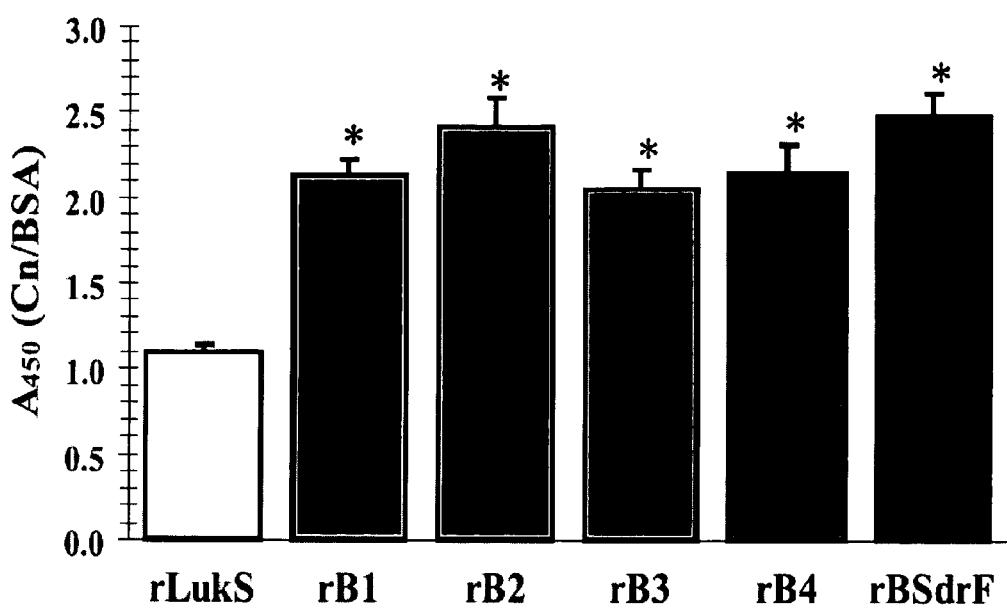
FIG. 5 illustrates binding of truncated forms of rBSdrF to immobilized type I collagen. Truncated forms of rBSdrF containing one of the four single B repeats were purified, biotinylated and their binding to type I collagen was tested. Purified rLukS was used as standard non-adherent control. Differential biotinylation amongst samples was obviated by expressing adherence as the ratio of A450 between collagen-coated wells vs. BSA-coated wells ($A_{450}$ Cn/BSA). Biotinylated adherent protein was detected with streptavidin conjugated with horseradish peroxidase. Data represent the mean plus standard error (S.E.) from at least three separate experiments (three microtiter wells per experiment). Truncated forms were named using single digits to indicate their B repeat position in the original rBSdrF. The concentration of biotinylated protein employed was 1 µg/ml. The symbol * indicates $p<0.05$ compared with rLukS.

Results showed that all four B repeats elicited a significant level of binding to type I Collagen (FIG. 5). These data suggest that all four B repeats are able to independently mediate adherence to type I Collagen.

Antibodies against the B Domain of SdrF Block the Adherence of rBSdrF and Reduce the Attachment of *S. epidermidis* to Collagen I. The specific anti-rBSdrF IgG fraction from a previously obtained rabbit antisera was purified. The effects of these specific IgGs on adherence to type I Collagen of both rBSdrF as well as *S. epidermidis* 9491 strain were then examined. Purified rBSdrF or *S. epidermidis* 9491 cells were pre-incubated with increasing concentrations of anti-rBSdrF IgGs for 1 h before being added to collagen-coated microplate wells. The purified specific anti-rBSdrF antibodies reduced the attachment of rBSdrF in a dose-dependent manner (FIG. 6A). In the same way, *S. epidermidis* 9491 attachment to type I Collagen was significantly reduced by anti-rBSdrF IgGs (FIG. 6B). In both cases purified preimmune IgGs had no perceptible effect (FIGS. 6A, 6B).

Figure 7:
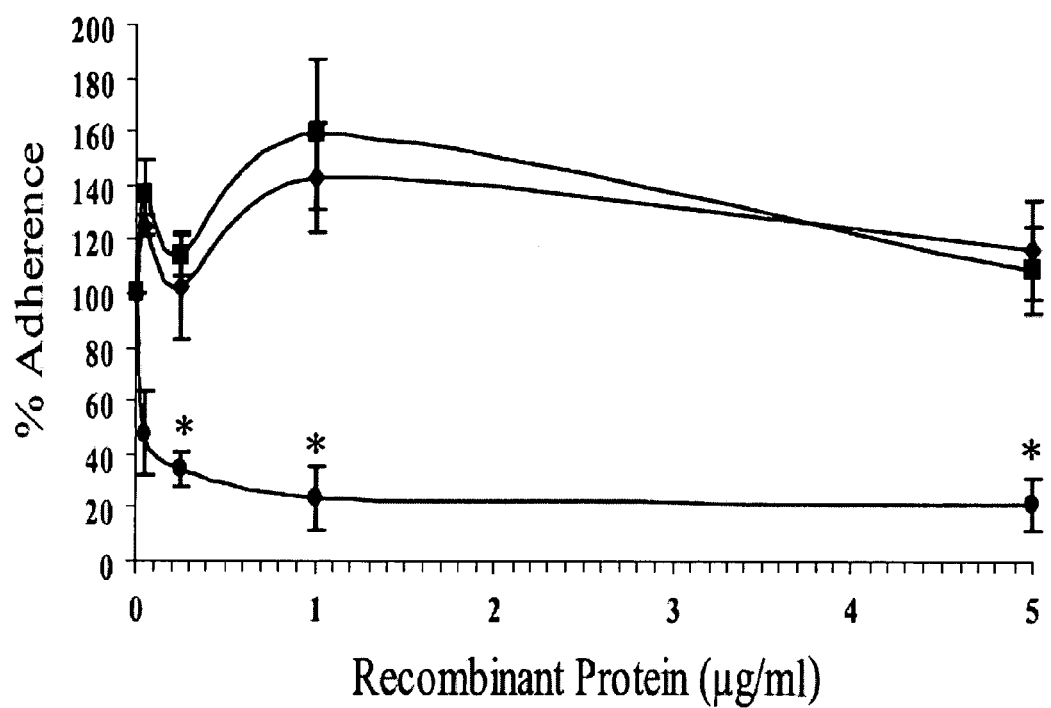
FIG. 7 shows that rBSdrF blocks binding of *S. epidermidis* to type I collagen. Collagen-coated wells (2.5 µg/ml) were preincubated with increasing concentrations of rLukS (filled diamonds, ♦), rASdrF (filled squares, ■), or rBSdrF (filled circles, ●) before the addition of *S. epidermidis* 9491 cells. Binding to PBS-preincubated wells was considered 100%. Data represent the mean plus S.E. from at least three separate experiments (three microtiter wells per experiment). The symbol * indicates that $p<0.05$ compared with control (PBS).
Figure 8:
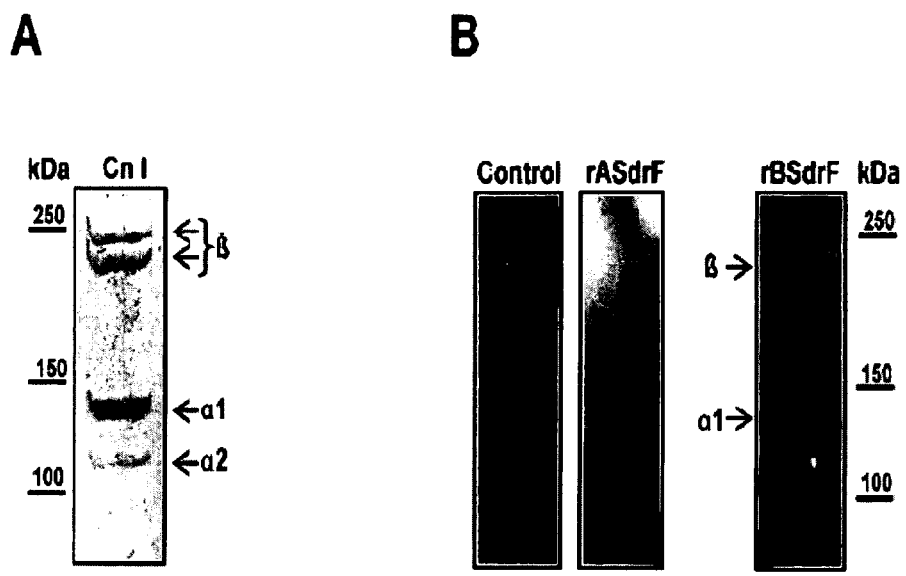
FIG. 8A-B show that rBSdrF attaches to the α1 chains of type I collagen.

Purified rBSdrF Reduces the Adherence of *S. epidermidis* to Collagen I. Collagen-coated microtiter wells were preincubated with increasing concentrations of either rLukS, rASdrF, or rBSdrF before incubation with *S. epidermidis* 9491 cells. Results showed that the presence of either rLukS or rASdrF did not produce any significant variation in the *S. epidermidis* attachment levels to type I Collagen (FIG. 7). However, rBSdrF caused a significant reduction in the adherence level of *S. epidermidis* 9491 cells to type I Collagen (FIG. 7).

rSdrF Binds both α1-and α1-chains of Collagen I. Type I collagen is typically composed of three polypeptide chains: two α1-chains and one α2-chain which, when analyzed by SDS-PAGE, result in a characteristic pattern of four bands distributed in two doublets with apparent molecular weights of 115 kDa and 130 kDa and another doublet at 215 kDa and 235 kDa (FIG. 8A) (Miller, E. J., and Rhodes, R. K. (1982) *Methods in Enzymology* 82 Pt A, 33-64). A Western ligand blot was prepared in which type I collagen was subjected to SDS-PAGE, transferred to a polyvinylidene difluoride membrane and incubated with purified rASdrF or rBSdrF. After incubation of type I collagen with rASdrF and rBSdrF, interactions were subsequently detected with the appropriate polyclonal antibodies (anti-rASdrF or anti-rBSdrF) followed by anti-rabbit IgG-peroxidase. No interaction between rASdrF and immobilized type I collagen was detected (FIG. 8B), confirming previous results indicating that this putative ligand binding domain does not adhere to type I Collagen. In contrast, incubation with purified rBSdrF produced a signal corresponding to the band formed by the two al-chains (FIG. 8B). This observation indicated that rBSdrF adheres to type I Collagen via one or both al-chains. Interestingly, rBSdrF did not appear bind to the blotted α2-chain (FIG. 8B). A second band was produced by rBSdrF that probably corresponds to one of the so called β-dimers (Miller, E. J., and Rhodes, R. K. (1982) *Methods in Enzymology* 82 Pt A, 33-64). To further investigate this observation both types of α-chains from type I Collagen were separately purified and these purified α-chains were tested to ascertain whether rBSdrF adhered to them using the previously mentioned solid phase assay of ligand-receptor interaction.

Figure 9:
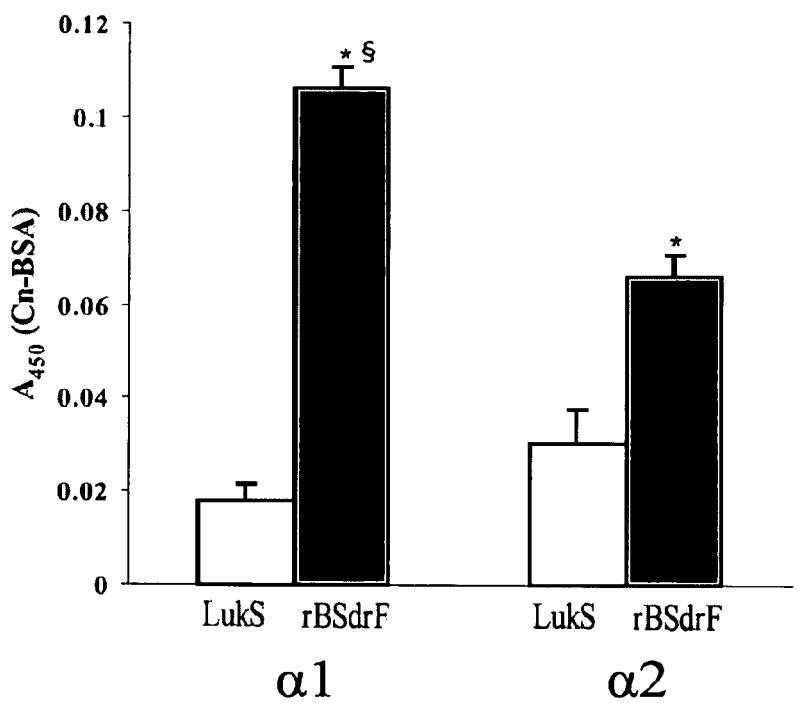
FIG. 9 illustrates that rBSdrF binds to both of the type I Collagen α1-and α2-chains. The type I Collagen α1- and α2-chains were separated, purified, and used to coat microtiter wells (20 µg/ml) before addition of biotinylated LukS or rBSdrF (1 µg/ml). Data represent the mean plus S.E. from at least three separate experiments (three microtiter wells per experiment). The symbol * indicates that $p<0.05$ compared with their respective controls (LukS). The symbol § indicates that $p<0.05$ compared with α2.
Figure 11A:
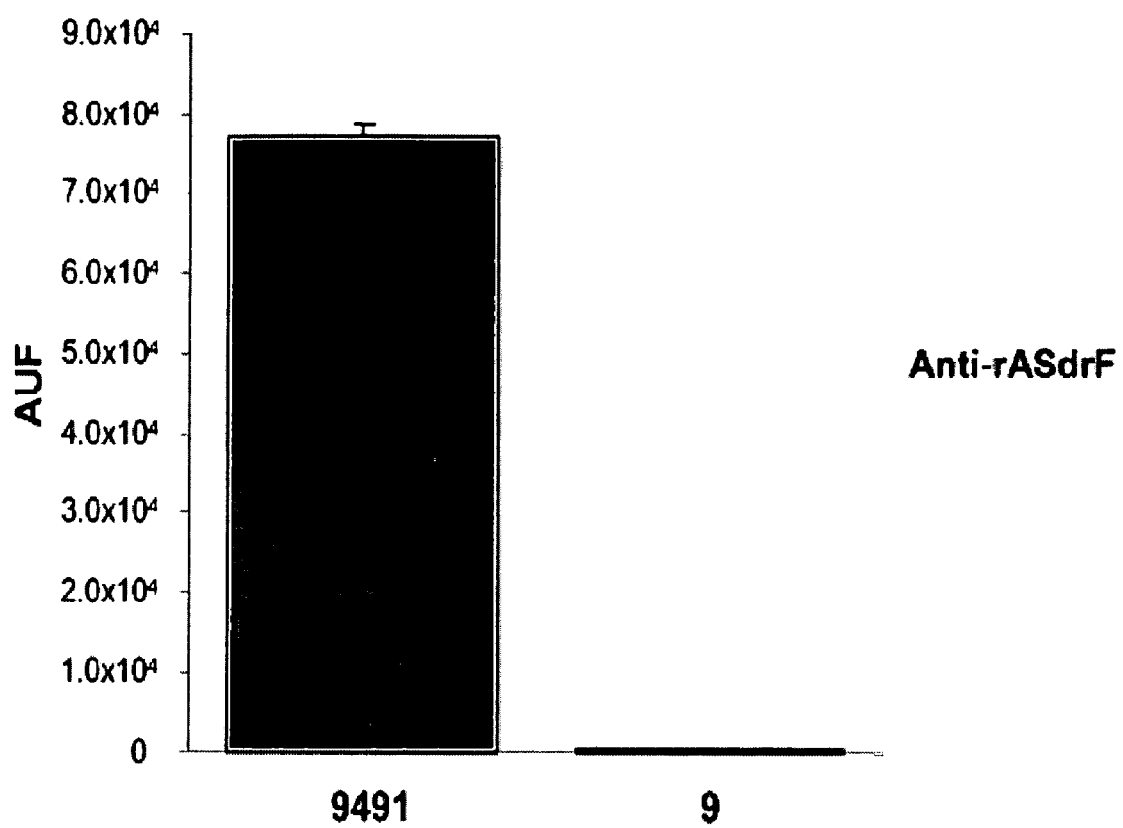
FIG. 11A-B illustrates that no cell surface expression of SdrF is detectable in *S. epidermidis* 9 as detected by flow cytometry analysis using *S. epidermidis* strain 9491 anti-rASdrF (FIG. 11A) and anti-rBSdrF (FIG. 11B) antibodies. As shown, large numbers of both anti-rASdrF (FIG. 11A) and anti-rBSdrF (FIG. 11B) antibodies bind cells of *S. epidermi*-
Figure 11B:
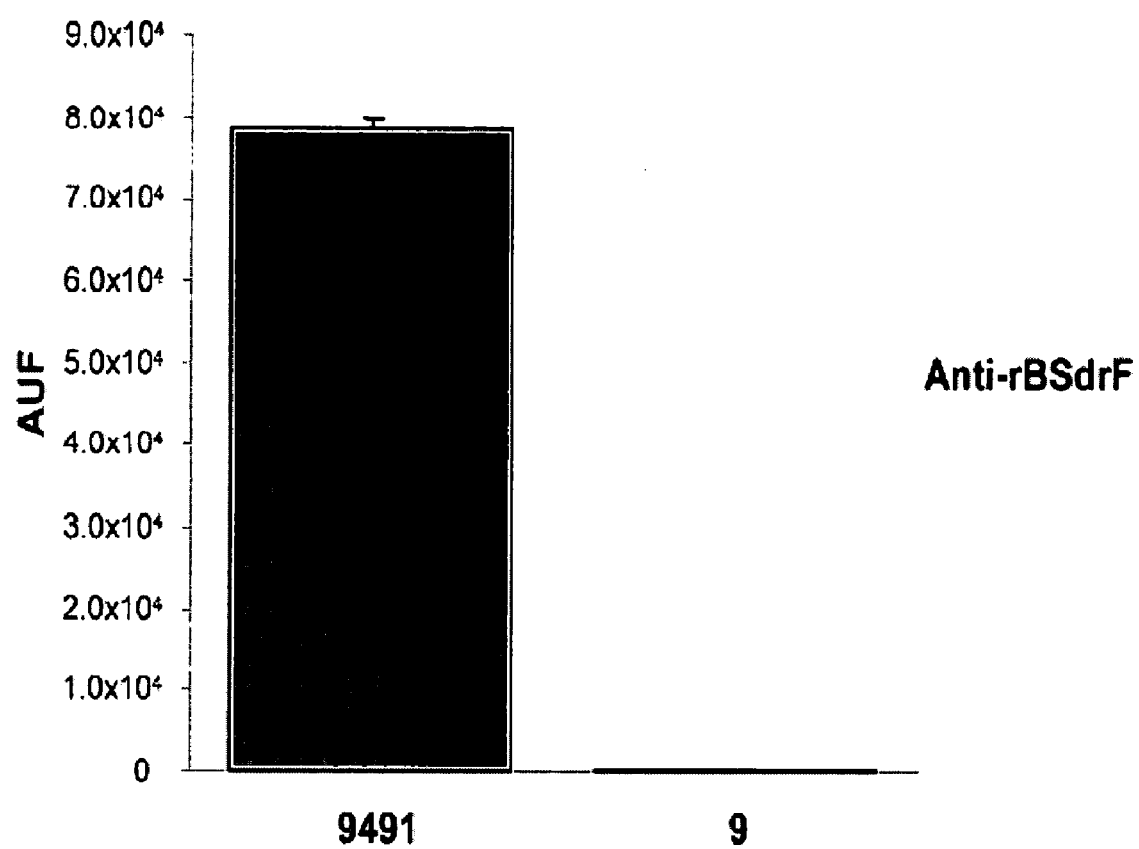

Interestingly, rBSdrF adhered to both α1-and α2-coated microtiter wells (FIG. 9). However, it was also observed that rBSdrF adheres with a significantly higher affinity to the α1 chain than to the α2-chain (FIG. 9).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. An isolated *Staphylococcus epidermidis* SdrF peptide consisting of any of SEQ ID NOs: 3-9, or 31.

2. A composition comprising a pharmaceutically acceptable carrier and the peptide of claim 1.

3. A method of treating or inhibiting *Staphylococcus epidermidis* infection in a mammal comprising administering to the mammal a composition comprising an isolated *Staphylococcus epidermidis* SdrF peptide consisting of any of SEQ ID NO:3-9, 31, or a combination thereof to thereby treat or inhibit *Staphylococcus epidermidis* infection in a mammal.

4. The method of claim 3, wherein the method inhibits *Staphylococcus epidermidis* colonization of a medical device in the mammal.

5. A composition comprising an isolated *Staphylococcus epidermidis* SdrF peptide consisting of any of SEQ ID NOS: 3-9, 31, or a combination thereof.

* * * * *

UNITED STATES PATENT AND TRADEMARK OFFICE
CERTIFICATE OF CORRECTION

PATENT NO. : 8,389,682 B2
APPLICATION NO. : 12/523425
DATED : March 5, 2013
INVENTOR(S) : Arrecubieta et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 466 days.

Signed and Sealed this
First Day of September, 2015

Michelle K. Lee
*Director of the United States Patent and Trademark Office*